(12) United States Patent
Roser et al.

(10) Patent No.: US 6,893,657 B2
(45) Date of Patent: May 17, 2005

(54) SOLID DOSE DELIVERY VEHICLE AND METHODS OF MAKING SAME

(75) Inventors: Bruce J. Roser, Cambridge (GB); Jaap Kampinga, Groningen (NL); Camilo Colaco, Cambridge (GB); Julian Blair, Cambridgeshire (GB)

(73) Assignee: Quadrant Drug Delivery Ltd. (GB)

( * ) Notice: Subject to any disclaimer, the term of this patent is extended or adjusted under 35 U.S.C. 154(b) by 176 days.

(21) Appl. No.: 10/376,136

(22) Filed: Feb. 27, 2003

(65) Prior Publication Data

US 2003/0147961 A1 Aug. 7, 2003

Related U.S. Application Data

(63) Continuation of application No. 09/945,180, filed on Aug. 31, 2001, now Pat. No. 6,565,871, which is a continuation of application No. 09/628,380, filed on Aug. 1, 2000, now Pat. No. 6,331,310, which is a continuation of application No. 08/349,029, filed on Dec. 2, 1994, now Pat. No. 6,290,991.

(51) Int. Cl.$^7$ .............................. A61K 9/48; A61K 9/20; A61K 9/14; A61F 2/02; A61F 6/06

(52) U.S. Cl. ...................... 424/451; 424/464; 424/489; 424/45; 424/46; 424/78.04; 424/423; 424/427; 430/434; 430/436; 430/449

(58) Field of Search ................................ 424/451, 464, 424/489, 45, 46, 78.04, 423, 427, 430, 434, 436, 449

(56) References Cited

U.S. PATENT DOCUMENTS

| | | |
|---|---|---|
| 979,993 A | 12/1910 | O'Bryne et al. |
| 1,855,591 A | 4/1932 | Wallerstein |
| 3,557,717 A | 1/1971 | Chivers |
| 3,619,294 A | 11/1971 | Black et al. |
| 3,632,357 A | 1/1972 | Childs |
| 3,655,442 A | 4/1972 | Schwer et al. |
| 3,745,682 A | 7/1973 | Waldeisen |
| 3,948,263 A | 4/1976 | Drake, Jr. et al. |
| 4,127,502 A | 11/1978 | Li Mutti et al. |
| 4,158,544 A | 6/1979 | Louderback |
| 4,244,949 A | 1/1981 | Gupta |
| 4,326,524 A | 4/1982 | Drake, Jr. et al. |
| 4,327,076 A | 4/1982 | Puglia et al. |
| 4,327,077 A | 4/1982 | Puglia et al. |
| 4,407,786 A | 10/1983 | Drake |
| 4,588,744 A | 5/1986 | McHugh |

(Continued)

FOREIGN PATENT DOCUMENTS

| | | |
|---|---|---|
| DE | 1080265 | 4/1960 |
| EP | 0111216 | 6/1984 |

(Continued)

OTHER PUBLICATIONS

Uedaira, Hatsuho, and Hisashi Uedaira (1980) "The Effect of Sugars on the Thermal Denaturation of Lysozyme" *The Chemical Society of Japan* 2451–2455.

(Continued)

*Primary Examiner*—Carlos A. Azpuru
(74) *Attorney, Agent, or Firm*—Saliwanchik, Lloyd & Saliwanchik

(57) ABSTRACT

The present invention encompasses a solid dose delivery vehicle for ballistic administration of a bioactive material to subcutaneous and intradermal tissue, the delivery vehicle being sized and shaped for penetrating the epidermis. The delivery vehicle further comprises a stabilizing polyol glass loaded with the bioactive material and capable of releasing the bioactive material in situ. The present invention further includes methods of making and using the solid dose delivery vehicle of the invention.

7 Claims, 10 Drawing Sheets

U.S. PATENT DOCUMENTS

| | | | |
|---|---|---|---|
| 4,591,552 A | 5/1986 | Neurath | |
| 4,620,847 A | 11/1986 | Shishov et al. | |
| 4,680,027 A | 7/1987 | Parsons et al. | |
| 4,684,719 A | 8/1987 | Nishikawa et al. | |
| 4,701,417 A | 10/1987 | Portenhauser et al. | |
| 4,790,824 A | 12/1988 | Morrow et al. | |
| 4,793,997 A | 12/1988 | Drake et al. | |
| 4,814,436 A | 3/1989 | Shibata et al. | |
| 4,824,938 A | 4/1989 | Koyama et al. | |
| 4,861,627 A | 8/1989 | Mathiowitz et al. | |
| 4,865,871 A | 9/1989 | Livesey et al. | |
| 4,883,762 A | 11/1989 | Hoskins | |
| 4,891,319 A | 1/1990 | Roser | |
| 4,906,463 A | 3/1990 | Cleary et al. | |
| 5,006,343 A | 4/1991 | Benson et al. | |
| 5,011,678 A | 4/1991 | Wang et al. | |
| 5,013,557 A | 5/1991 | Tai | |
| 5,026,566 A | 6/1991 | Roser | |
| 5,149,653 A | 9/1992 | Roser | |
| 5,204,108 A | 4/1993 | Illum | |
| 5,239,993 A | 8/1993 | Evans | |
| 5,240,843 A | 8/1993 | Gibson et al. | |
| 5,270,048 A | 12/1993 | Drake | |
| 5,284,656 A | 2/1994 | Platz et al. | |
| 5,290,765 A | 3/1994 | Wettlaufer et al. | |
| 5,306,506 A | 4/1994 | Zema et al. | |
| 5,312,335 A | 5/1994 | McKinnon et al. | |
| 5,348,852 A | 9/1994 | Bonderman | |
| 5,354,562 A | 10/1994 | Platz et al. | |
| 5,354,934 A | 10/1994 | Pitt et al. | |
| 5,422,384 A | 6/1995 | Samuels et al. | |
| 5,425,951 A | 6/1995 | Goodrich, Jr. et al. | |
| 5,512,547 A | 4/1996 | Johnson et al. | |
| 5,589,167 A | 12/1996 | Cleland et al. | |
| 5,591,453 A | 1/1997 | Ducheyne | |
| 5,997,848 A | 12/1999 | Patton | |
| 6,290,991 B1 * | 9/2001 | Roser et al. | 424/502 |
| 6,331,310 B1 * | 12/2001 | Roser et al. | 424/423 |

FOREIGN PATENT DOCUMENTS

| | | |
|---|---|---|
| EP | 0139286 | 5/1985 |
| EP | 0140489 | 5/1985 |
| EP | 0229810 | 1/1987 |
| EP | 0297887 | 1/1989 |
| EP | 0415567 | 3/1991 |
| EP | 0433679 | 6/1991 |
| EP | 0520748 | 12/1992 |
| EP | 0714905 | 6/1993 |
| EP | 0357665 | 3/1994 |
| EP | 0383569 | 5/1994 |
| EP | 0601965 | 6/1994 |
| ES | 2009704 | 1/1989 |
| FR | 2238476 | 3/1975 |
| GB | 1381588 | 1/1975 |
| GB | 1533012 | 11/1978 |
| GB | 083464 | 3/1982 |
| GB | 2126588 | 3/1984 |
| GB | 2206273 | 1/1989 |
| JP | 58216695 | 12/1983 |
| JP | 60244288 | 12/1985 |
| JP | S5597096 | 9/1988 |
| JP | 65502592 | 9/1988 |
| WO | 8604095 | 7/1986 |
| WO | 8700196 | 1/1987 |
| WO | 8705300 | 9/1987 |
| WO | 8808298 | 11/1988 |
| WO | 8906542 | 7/1989 |
| WO | 9005182 | 5/1990 |
| WO | 9011756 | 10/1990 |
| WO | 9116038 | 10/1991 |
| WO | 9118091 | 11/1991 |
| WO | 9202133 | 2/1992 |
| WO | 9300951 | 1/1993 |
| WO | 9302834 | 2/1993 |
| WO | 9309832 | 5/1993 |
| WO | 9310756 | 6/1993 |
| WO | 9310758 | 6/1993 |
| WO | 9311220 | 6/1993 |
| WO | 9323110 | 11/1993 |
| WO | 9407514 | 4/1994 |
| WO | 9408552 | 4/1994 |
| WO | 9413271 | 6/1994 |
| WO | 9422423 | 10/1994 |
| WO | 9424263 | 10/1994 |
| WO | 9500127 | 1/1995 |
| WO | 9506126 | 3/1995 |
| WO | 9523613 | 9/1995 |
| WO | 9524183 | 9/1995 |
| WO | 9531479 | 11/1995 |
| WO | 9533488 | 12/1995 |
| WO | 9640049 | 12/1996 |

OTHER PUBLICATIONS

Carpenter, John F. and John H. Crowe (1988) "Modes of Stabilization of a Protein by Organic Solutes" *Cryobiology* 25:459–470.

Levine, Harry and Louise Slade (1988) "Principles of "Cryostabilization" Technology from Structure/Property Relationships of Carbohydrate/Water Systems—A Review" *Cryo–Letters* 9:21–63.

Burke, Michael J. Appendix D: The Glassy State and Survival of Anhydrous Biological Systems, 358–363.

Townsend, Michael W. and Patrick P. DeLuca (1988) "Use of Lyoprotectants in the Freeze–Drying of a Model Protein, Ribonuclease A" *Journal of Parenteral Science & Technology* 42(6):190–199.

James M. Flink "Structure and Structure Transitions in Dried Carbohydrate Materials" In: Physical Properties of Foods, M. Peleg and E.B. Bogley (editors), 1983, Aui Publishing.

Herrington, D.L. (1934) In: Some Physico–Chemical Properties of Lactose, pp. 501–518.

White, G.W. and S.H. Cakebread (1966) "The glassy state in certain sugar–containing food products" *J. Fd. Technol.* 1:73–82.

Levine, H. and Louise Slade (1988) "Collapse Phenomena—A Unifying Concept For Interpreting The Behaviour Of Low Moisture Foods" *In: Food Structure—Its Creation and Evaluation*, (eds.) J.M. Blanshard, J.R. Mitchell Bullinicrilts, p. 149–180.

Kauzmann, Walter (1948) "The Nature of the Glassy State and the Behavior of Liquids at Low Temperatures" pp. 219–256.

Levine, Harry and Louise Shade (1986) "A Polymer Physico–Chemical Approach to the Study of Commercial Starch Hydrolysis Products (SHPs)" *Carbohydrate Polymers* 6:213–244.

Carpenter, John F., Beth Martin, Lois M. Crowe, John H. Crowe (1987) "Stabilization of Phosphofrucktokinase during Air–Drying . . . and Sugar/Transition Metal Mixtures" *Cryobiology* 24:455–464.

Schneider, Z. A. Stroinski, J. Pawelkiewicz (1968) "Thermostability of Enzyme in the Three–dimensional Network of Polysaccharide Chains" Bulletin De L'Academie Polonaise Des Sciences CL. II. vol. XVI, No. 4, pp. 203–204.

Van de Beek, M. J., and S. Y. Gerisma (1969) "Preservation of the Enzymatic Activity of Rennin During Spray Drying And During Storage And The Effect Of Sugars And Certain Other Additives" *Neth. Milk Dairy J.* 23:46–54.

The Condensed Chemical Dictionary, 7th Edition, 1986, revised by Arthur and Elizabeth Rose, State College, Pa., Reinhold Publishing Corporation, New York, p. 448.

Water Relations of Foods, Proceedings of an International Symposium, Glasgow, Sep. 1974, edited by R.B. Duckworth, Academic Press, pp. 648–649.

The New Encyclopaedia Britannica (1985), vol. 16, 15th Edition, pp. 476–479.

Poole, P.L. and J.L. Finney (1983) "Hydration–induced conformational and flexibility changes inlysozyme at low water content" *Int. J. Biol. Macromol.* 5:308–310.

Poole, P.L. and J. L. Finney (1983) "Sequential Hydration of a Dry Globular Protein" *Biopolymers* 22:255–260.

Finney, J.S. and P.L. Poole (1984) "Protein Hydration and Enzyme Activity: The Role of Hydration–Induced Conformation and Dynamic Changes in the Activity of Lysozyme" *Comments Mol. Cell. Biophys.* 2(3/4), 129–151.

S. Bone, R. Pethig (1985) "Dielectric Studies of Protein Hydration and Hydration–induced Flexibility" *J. Mol. Biol.* 181:323–326.

Williams, Malcolm, Robert F. Landel and John D. Ferry (1955) "The Temperature Dependence of Relaxation Mechanisms in Amorphous Polymers and Other Glass–forming Liquids" *Temperature Dependence Of Relaxation Mechanisms* 77:3701–3707.

To, Eddie C. and James M. Flink (1978) "Collapse, a structural transition in freeze dried *carbohydrates*" *J. Fd Technol.* 13:567–581.

Labrude, P., M. Rasolomanana, C. Vigneron, C. Thirion, and B. Chaillot (1989) "Protective Effect of Sucrose on Spray Drying of Ocxyhemoglobin" *Journal of Pharmaceutical Sciences* 78(3):223–229.

Labrude et al (1988), "Atomisation d'oxyhémoglobine en présence de saccharose: Etude par dichroïsme circulaire et résonance paramagnétique électronique: Comparaison avec la lyophilisation," *S.T.P. Pharma* 4(6):472–480.

"Tg Measurements".

Skrabanja et al. (1994). "Lyophilization of Biotechnology Products," *PDA Journal* 48(6):311–317.

Brochure, *Permazyme Technology*, Pafra Biopreservation.

Pikal, M.J., and Shah, S. (1990), "Moisture Transfer from Stopper to Product and Resulting Stability Implications," International Symposium on Biological Product Freeze–Drying and Formulation, Bethesda, USA, in *Developments in Biological Standardization* 74 (International Association of Biological Standardization, Joan C. May and F. Brown, Acting Ed.).

Pharmacla LKB Biotechnology advertisement for Ready–to–Go DNA Labelling Kit.

Ready–to–Go™ Molecular Biology Reagents: "PurePrep™ *Macro* Plasmid Purification Kit," "Overview: Ready–to–Go™ Technology," and "Ready–to–Go™ Lambda Packaging Kit," Pharmacia Biotech, *Analects* 2:1–7 (Spring 1994).

Green, J.L., and Angell, C.A. (1989), "Phase Relations and Vitrification in Saccharide–Water Solutions and the Trehalose Anomaly," *J. Phys. Chem.* 93:2880–2882.

Levine, Harry and Louise Slade (1992) "Another view of Trehalose for Drying and Stabilizing Biological Materials" 36–40.

Naini et al. (1994), "Physical Characterization of Spray Dried Sugars Suitable as Carriers in Inhalation Systems," Poster Presentation, Tenth Annual AAPS, Miami, FL.

Roos, Y. (1993), "Melting and glass transitions of low molecular weight carbohydrates," *Carbohydrate Research* 238:39–48.

Klein et al.(1987) "High Velocity Microprojectiles for Delivering Nucleic Acids into Living Cells" *Nature* 327:70–73.

Vain et al.(1993) "Development of the Practive Inflow Gun" *Plant Cell, Tissue and Organ Culture* 33:237–246.

Sanchez et al. (1989) "Recombinant System for Overexpression of Cholera Toxin B Subunit in *Vibrio cholera* as a Basis for Vaccine Development" *Proc Natl Sci USA* 86:481–485.

Takahashi et al. (1990) "Induction of $CD8^+$ Cytotoxic T Cells by Immunization with Purified HIV–1 Envelope Protein in ISCOMs" *Nature* 344:873–875.

Blakelay et al. (1990) "Dry Instant Blood Typing Plate for Bedside Use" *Lancet* 336:854–855.

Roser (1991) "Trehalose, a New Approach to Premium Dried Foods" *Trends in Food Sci & Tech* pp. 166–169.

Colaco et al. (1992) "Trehalose Stabilisation of Biological Molecules" *Biotechnol Internet* pp. 345,347–350.

Roser et al. (1991) "Trehalose Drying: A Novel Replacement for Freeze Drying" *Biopharm* 4:47–53.

Colaco et al.(1992) "Extraordinary Stability of Enzymes Dried In Trehalose: Simplified Molecular Biology" *Bio/Tech* 10:1007–1011.

Roser et al. (1993) "A Sweeter Way to Fresher Food" *New Scientist* pp. 25–28.

Pekarek et al. (1994) "Double–walled Polymer Microspheres for controlled Drug Release" *Nature* 367:258–260.

Jovanolo–Peterson et al. (1993) "Jet–Injected Insulin is Associated with Decreased Antibody Production and Postprandial Glucose Variability When Compared with Needle–Injected Insulin in Gestational Diabetic Women" *Diabetes Care* 16:1479–1484.

Lindberg (1993) "Creating the Future for Portable Inhalers" *Summary of Lecture at Management Forum* pp. 1–2.

Colaco et al. (1992) *Chemical Abstracts* 118:#164103.

Roser (1991) *Chemical Abstracts* 116: #127053.

Roser (1991) *Chemical Abstracts* 116: #54989.

Roser et al. (1991) *Chemical Abstracts* 116: #124367.

Roser (1990) *Chemical Abstracts* 115:#142247.

Roser (1989) *Chemical Abstracts* 113: #29245.

Roser (1986) *Chemical Abstracts* 107: #20354.

Hahn et al. (1989) "Solid Surfactant Solutions of Active Ingredients in Sugar Esters" *Pharmaceutical Research* 6:958–960.

Dialog® English Abstract of JP 58–216695 (Dec. 16, 1983).

Dialog® English Abstract of FR 2238476 (Mar. 28, 1975).

Dialog® English Abstract of JP 63–502592 (Sep. 29, 1988).

Letter from Bruce J. Roser to Raj Uppal (Aug. 14, 1997).

Letter form Kevin Appleton to Susan Lehnhardt, including index of art produced by Bruce J. Roser (Sep. 22, 1997).

Dialog® Search for references cited in letter from Bruce J. Roser to Raj Uppal (Aug. 14, 1997), 6 pages total.

Dialog® Search for Solidase Injection Devices, pp. 49–99 (Aug. 23, 1995).

Sakuri, Y. (Eds), "Food General Dictionary" Sixth Edition, (English translation is 10 pages total).

Reasons for Opposition, (1995) 5 pages total.

Supplement of Reasons for Opposition, (Dec. 31, 1995), 23 pages total.

Grounds for Rejection, (1995) 6 pages total.

Kanna et al. (1974) "Denaturation of Fish Muscle Protein by Dehydration–V," *Bull Tokai Reg Fish Res Lab* 77:1–17.

Derwent® WPI File 351 Abstract of PCT WO 87/05300 (Sep. 11, 1987).

Derwent® WPI Abstract of JP 8298125 (Jun. 7, 1982).

Decision re JP 63–505533 (Japanese date of Apr. 12, 1998) (English translation to be disclosed at a later date).

Fax and product information regarding Stop n Grow, (Jun. 26, 1997).

Letter from David T. Walsh to Dr. A. Tunnacliffe (Nov. 16, 1995).

Quadrant Healthcare plc Invention Report and Record (Oct. 3, 1996).

"Development of a Dry and Thermostable Oral Pollo Vaccine," Progress Report QHCL, RIVM and RUG, May 1993–Oct. 1993, (Apr. 22, 1997), 11 pages total.

"Development of a Dry and Thermostabe Oral Pollo Vaccine," Progress Report QHCL and RIVM, Nov. 1993–Apr. 1994, (Apr. 22, 1994), 11 pages total.

Wang et al. (eds.) (1993) "Stability and Characterization of Protein and Peptide Drugs" Table of Contents Enclosed Herewith.

Skrabanja et al. (1994) "Lyophilization of Biotechnology Products" *PDA J Pharm Sci Technol* 48:311–317.

Timko et al. (1984) "Thermal Analysis Studies of Glass Dispersion Systems" *Drug Devel Ind Pharm* 10:425–451.

Roser (1990) *Chemical Abstracts* 115:#142247.

Roser (1989) *Chemical Abstracts* 113: #29245.

Roser (1986) *Chemical Abstracts* 107: #20354.

Hahn et al. (1989) "Solid Surfactant Solutions of Active Ingredients In Sugar Esters" *Pharmaceutical Research* 6:958–960.

Dialog® English Abstract of JP 58–216695 (Dec. 16, 1983).

Dialog® English Abstract of FR 2238476 (Mar. 28, 1975).

Dialog® English Abstract of JP 63–502592 (Sep. 29, 1988).

Letter from Bruce J. Roser to Raj Uppal (Aug. 14, 1997).

Handbook of Natural Material for Food Processing, Ninth Edition (English translation to be disclosed at a later date), pp. 384.

Chemical Dictionary, 7$^{th}$ Edition (English translation to be disclosed at a later date), pp. 310–311.

\* cited by examiner

SAMPLES MEASURED AT QUADRANT
SYMPATEC HELOS Particle size analysis

| | | | | | | | | |
|---|---|---|---|---|---|---|---|---|
| Measure method | dry disperser | | (RODOS) | | Cascade | no | | |
| Pressure | 3.0 bar | | | Injector depression | | max | mbar | |
| Feed rate | % | | | Rotation rate | | | % | |
| Focal length | = 100 mm | | Date | | 22/07/94 / | 11:59 | | |
| Measuring time | = 1 s | | Filename | | C:\H_DATA\QUADRANT\SAMP4_01.HP | | | |
| Operator | = LAKE | | | | | | | |
| Measuring time | = SAMPLE 4  0.5M Trehalose + 0.5M Ca Lactate | | | | | | | |
| Comments1 | | | | LABPLANT SPRAY DRIER (of Sample 1) | | | | |
| Comments2 | | | | | | | | |

| xo/mym | Q3/% | I | xo/mym | Q3/% | I | xo/mym | Q3% | I | xo/mym | Q3/% |
|---|---|---|---|---|---|---|---|---|---|---|
| | | I | 3.10 | 10.39 | I | 12.50 | 74.19 | I | 51.00 | 100.00 |
| 0.90 | 1.41 | I | 3.70 | 13.85 | I | 15.00 | 84.27 | I | 61.00 | 100.00 |
| 1.10 | 2.10 | I | 4.30 | 17.78 | I | 18.00 | 91.90 | I | 73.00 | 100.00 |
| 1.30 | 2.79 | I | 5.00 | 22.82 | I | 21.00 | 96.10 | I | 87.00 | 100.00 |
| 1.50 | 3.48 | I | 6.00 | 30.48 | I | 25.00 | 98.68 | I | 103.00 | 100.00 |
| 1.80 | 4.56 | I | 7.50 | 42.17 | I | 30.00 | 99.78 | I | 123.00 | 100.00 |
| 2.20 | 6.13 | I | 9.00 | 53.30 | I | 36.00 | 100.00 | I | 147.00 | 100.00 |
| 2.60 | 7.89 | I | 10.50 | 63.24 | I | 43.00 | 100.00 | I | 175.00 | 100.00 |

| | | | | | | | |
|---|---|---|---|---|---|---|---|
| x10 | = | 3.02 mym | x50 | = | 8.56 mym | x90 = | 17.25 mym |
| x5 | = | 1.91 mym | x16 | = | 4.03 mym | x84 = | 14.93 mym |
| Sv= | | 1.08 m2/cm3 | | | c_opt= 2.4 % | | |

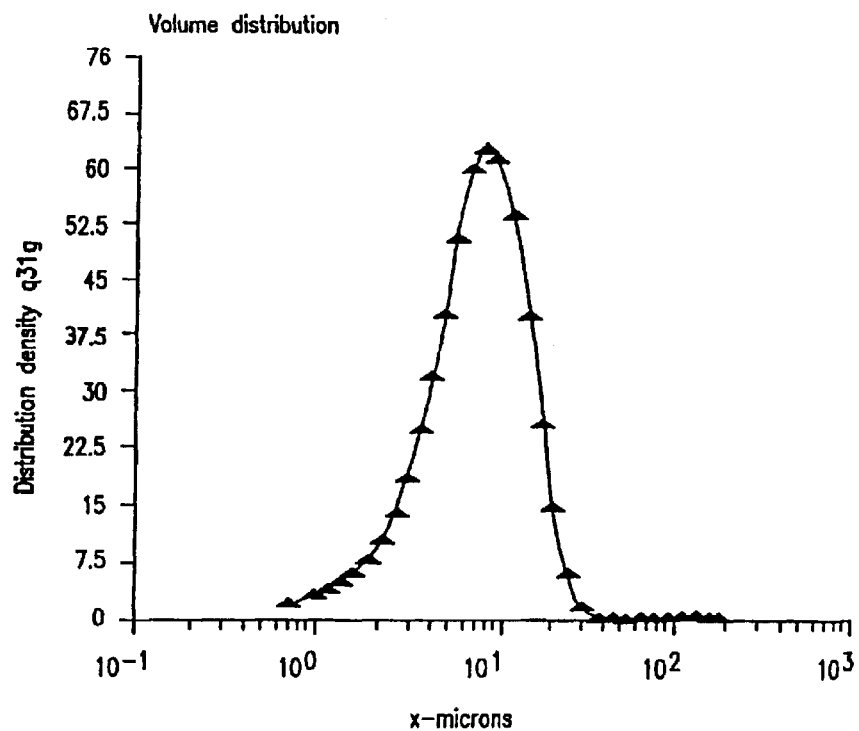

FIG. 3

SOLID DOSE DELIVERY VEHICLE AND METHODS OF MAKING SAME

CROSS-REFERENCE TO A RELATED APPLICATION

This application is a continuation of application Ser. No. 09/945,180, filed Aug. 31, 2001 now U.S. Pat. No. 6,565,871; which is a continuation of application Ser. No. 09/628,380, filed Aug. 1, 2000, now U.S. Pat. No. 6,331,310; which is a continuation of application Ser. No. 08/349,029, filed Dec. 2, 1994, now U.S. Pat. No. 6,290,991.

FIELD OF THE INVENTION

The present invention relates generally to solid dose vehicles for delivery of bioactive materials and, more specifically, to solid dose delivery vehicles comprising a stabilizing polyol and a bioactive material. Methods of their making and uses thereof are also provided.

BACKGROUND OF THE INVENTION

Solid dose delivery of bioactive materials to mucosal, dermal, ocular, subcutaneous, intradermal and pulmonary tissues offers several advantages over previous methods such as topical applications of liquids, transdermal administration via so-called "patches" and hypodermic injection. In the case of injection, solid dose delivery can reduce the risk of infection by eliminating the use of needles and syringes, provide for more accurate dosing than multidose vials, and minimize or eliminate the discomfort which often attends hypodermic injection. Several solid dose delivery systems have been developed including those utilizing transdermal and ballistic delivery devices.

Topical delivery is utilized for a variety of bioactive materials such as antibiotics for wound healing. These topical ointments, gels, creams, etc. must be frequently reapplied in order to remain effective. This is particularly difficult in the case of burn wounds.

Devices used for administering drugs transdermally usually comprise laminated composites with a reservoir layer of drug with the composite being adhered to the skin, i.e., transdermal patch, such as described in U.S. Pat. No. 4,906,463. However, many drugs are not suitable for transdermal delivery, nor have transdermal drug release rates for those capable of transdermal delivery been perfected.

Subdermal implants have also been formulated for slow release of certain pharmaceutical agents for extended periods of time such as months or years. A well-known example is the Norplant® for delivery of steroid hormones. Such implants are usually constructed of an inner, drug-filled core which is relatively permeable to the drug and an outer matrix which is relatively impermeable to the drug. Both inner core and outer matrix are generally formed from polymers. The implants release drugs by dissolution of the drug in the inner core and slow release across the outer matrix. The inner core may substantially dissolve over time, however, in devices currently in use, the outer matrix does not dissolve. Implants are placed subcutaneously by making an incision in the skin and forcing the implants between the skin and the muscle. At the end of their use, if not dissolved, these implants are surgically removed. U.S. Pat. No. 4,244,949 describes an implant which has an outer matrix of an inert plastic such as polytetrafluoroethylene resin. PCT/GB 90/00497 describes slow release vitreous systems for formation of implantable devices. These implants are bioabsorbable and need not be surgically removed. However, insertion is by surgical means. Moreover, these devices may be limited in the type of bioactive material that can be incorporated. In the case of polymeric implants, bioactive materials that cannot withstand organic solvents are not suitable for use. In the case of vitreous systems, bioactive materials that cannot withstand the elevated temperatures necessary to form the implants are unsuitable for use. In all cases, bioactive materials that are unstable at body temperature, particularly over long time periods, are unsuitable for use.

A variety of formulations have been provided for administration in aerosolized form to mucosal surfaces, particularly "by-inhalation" (naso-pharyngeal and pulmonary). Compositions for by-inhalation pharmaceutical administration generally comprise a liquid formulation of the pharmaceutical agent and a device for delivering the liquid in aerosolized form. U.S. Pat. No. 5,011,678 describes suitable compositions containing a pharmaceutically active substance, a biocompatible amphophilic steroid and a biocompatible (hydro/fluoro) carbon propellant. U.S. Pat. No. 5,006,343 describes suitable compositions containing liposomes, pharmaceutically active substances and an amount of alveolar surfactant protein effective to enhance transport of the liposomes across a pulmonary surface.

One drawback to the use of aerosolized formulations is that maintenance of pharmaceutical agents in aqueous suspensions or solutions can lead to aggregation and loss of activity and bioavailability. The loss of activity can be partially prevented by refrigeration; however, this limits the utility of these formulations. This is particularly true in the case of peptides and hormones. For instance, synthetic gonadotropin releasing hormone (GnRH) analogs, such as the agonist nafarelin or the antagonist ganirelex are designed for high potency, increased hydrophobicity and membrane binding. The compounds have sufficient hydrophobic character to aggregate in aqueous solution and to form an ordered structure that increases in viscosity with time. Thus bioavailability in nasal or pulmonary formulations may be prohibitively low. The use of powdered formulations overcomes many of these drawbacks. The requisite particle size of such powders is 0.5–5 microns in order to attain deep alveolar deposition in pulmonary delivery. Unfortunately, powders of such particle size tend to absorb water and clump and thus diminish deposition of the powder in the deep alveolar spaces. Although powders with larger particle size are suitable for delivery to the naso-pharynx region, the tendency of powders to clump decreases the available particle surface area for contact with, and absorption through, these membranes. Devices which disaggregate clumps formed by electrostatic interactions are currently in use (e.g., the Turbohaler™); however, these do not disaggregate moisture induced clumps and it would be advantageous to have powders which do not absorb moisture and clump and thus increase the effective pulmonary concentration of the drug.

Solid dose delivery vehicles for ballistic, transdermal, administration have also been developed. For example, in U.S. Pat. No. 3,948,263, a ballistic animal implant comprised of an exterior polymeric shell encasing a bioactive material is described for veterinary uses. Similarly, in U.S. Pat. No. 4,326,524, a solid dose ballistic projectile comprising bioactive material and inert binder without an exterior casing is disclosed. Delivery is by compressed gas or explosion. Gelatin covered tranquilizing substances carried by ballistic projectiles for implant are also described in U.S. Pat. No. 979,993.

The above-described ballistic devices, however, are suited to large animal veterinary applications due to their relatively large size, on the order of millimeters. Ballistic delivery at the cellular level has also been successful. The general principle of ballistic administration is the use of a supersonic wavefront, created by the release of compressed gas, to propel the particles contained in an adjoining chamber. For example, nucleic acids adsorbed on tungsten microprojectile particles have been successfully delivered to living epidermal plant cells. See Klein *Nature* 327:70–73 (1987). A better controlled device is the particle inflow gun (PIG). Vain et al. (1993) Plant Cell, Tissue and Organ Culture 33:237–246. Devices have been described which fire ampules containing medication using gas pressure. U.S. Pat. No. 4,790,824; and PCT/GB 94/00753. Several devices that inject fluids have also been described. U.S. Pat. Nos. 5,312,335 and 4,680,027. There are few existing formulations suitable for ballistic delivery. Powder formulations of pharmaceuticals in their present form are unsuitable for ballistic administration. Particles of available powder forms are generally irregular, varying in size, shape and density. This lack of uniformity leads to powder deposit and loss at the skin surface during administration, as well as problems in control and consistency of the depth of delivery to subcutaneous and intradermal tissues.

Thus it would be advantageous to provide solid dose drug delivery vehicles of defined size, shape and density, to ensure more uniform distribution. Additional benefits would accrue if the shape of the vehicle could be controlled to facilitate or control penetration of the epidermis and hard layers of the skin. Small delivery vehicle size, preferably coupled with high momentum delivery, would also increase the comfort of administration and minimize tissue damage. The manufacture of such a solid dose delivery vehicle should be such that neither the delivery vehicle nor the bioactive substance being delivered is damaged nor its efficacy decreased. Furthermore, the bioactive substance should remain stable when loaded within or on the vehicle so that efficacious administration can be achieved, and to facilitate storage of the loaded delivery vehicle. Manufacture of the solid dose delivery vehicle and its loading with bioactive material and the administration of the vehicle should also be relatively simple and economical.

All references cited herein are hereby incorporated by reference.

SUMMARY OF THE INVENTION

The present invention encompasses a solid dose delivery vehicle suitable for therapeutic administration of a wide variety of substances, comprising a stabilizing polyol and a bioactive material. Preferred buffers, adjuvants and additional stabilizers are also provided. The delivery vehicle can be sized and shaped for a variety of modes of administration.

The invention further includes a solid dose delivery vehicle comprising an outer portion comprising a water soluble glassy and/or polymeric material having a hollow compartment therein, and an inner portion residing in the compartment, the inner portion comprising at least one stabilizing polyol and a therapeutically effective amount of at least one bioactive substance.

The invention also encompasses methods of delivering a bioactive material by providing a solid dose delivery vehicle described above and administering the vehicle to the tissue. Administration can be by mucosal, oral, topical, subcutaneous, intradermal and by-inhalation.

The invention further encompasses methods of making the solid dose delivery vehicle. The stabilizing polyol, bioactive material and any other components are mixed and processed by a wide variety of methods, including milling, spray drying, freeze drying, air drying, vacuum drying, fluidized-bed drying, co-precipitation and critical fluid extraction. The dried components can be heated to fluidize the glass which can then be drawn or spun into solid or hollow fibers. The dried components can also be mixed in aqueous or organic solutions and dried, such as by spray drying, freeze drying, air-drying, vacuum drying, fluidized-bed drying, co-precipitation and critical fluid extraction.

The invention further provides methods of making vehicles suitable for slow or pulsatile release of bioactive substances. The methods include combining bioactive material in solid solutions in stabilizing glass-forming polyol and other glass formers with dissolution or degradation rates slower than that of the glass-forming polyol, and processing the components as described above. The ratio of materials can be controlled so as to provide a wide range of narrowly defined release rates. The coformulations of stabilizing polyol and other water-soluble and/or biodegradable glasses, plastics and glass modifiers produced thereby are also encompassed by the present invention.

The invention further provides methods of making delivery vehicles of glasses of hydrated carbohydrates hydrates with increased Tg and the compositions obtained thereby. The method comprises adding a modifier, preferably a protein, in an amount sufficient to elevate the Tg, to the carbohydrate and processing according to a method described herein. The modifier may be an inert material or may be the bioactive material. The product obtained may be combined with stabilizing polyols with a Tg less than that of the modified carbohydrate to form a slow and/or pulsatile delivery system.

The vehicles and methods of the invention also encompass vehicles which comprise fibers, spheres, particles and needles. Preferably these vehicles are fibers, spheres, particles and needles. The vehicles can be either microscopic or macroscopic.

A wide variety of bioactive materials are suitable for use in accord with the present invention, including, but not limited to, therapeutic and prophylactic agents. The delivery vehicle and methods of the present invention provide for a variety of dosing schemes for delivery of the bioactive material and are suitable for both veterinary and human applications.

BRIEF DESCRIPTION OF THE DRAWINGS

FIG. 3 is a graph depicting the sharp particle size distribution for trehalose glass powder obtained by spray-drying in a Lab-plant spray dryer.

DETAILED DESCRIPTION OF THE INVENTION

Figure 1:
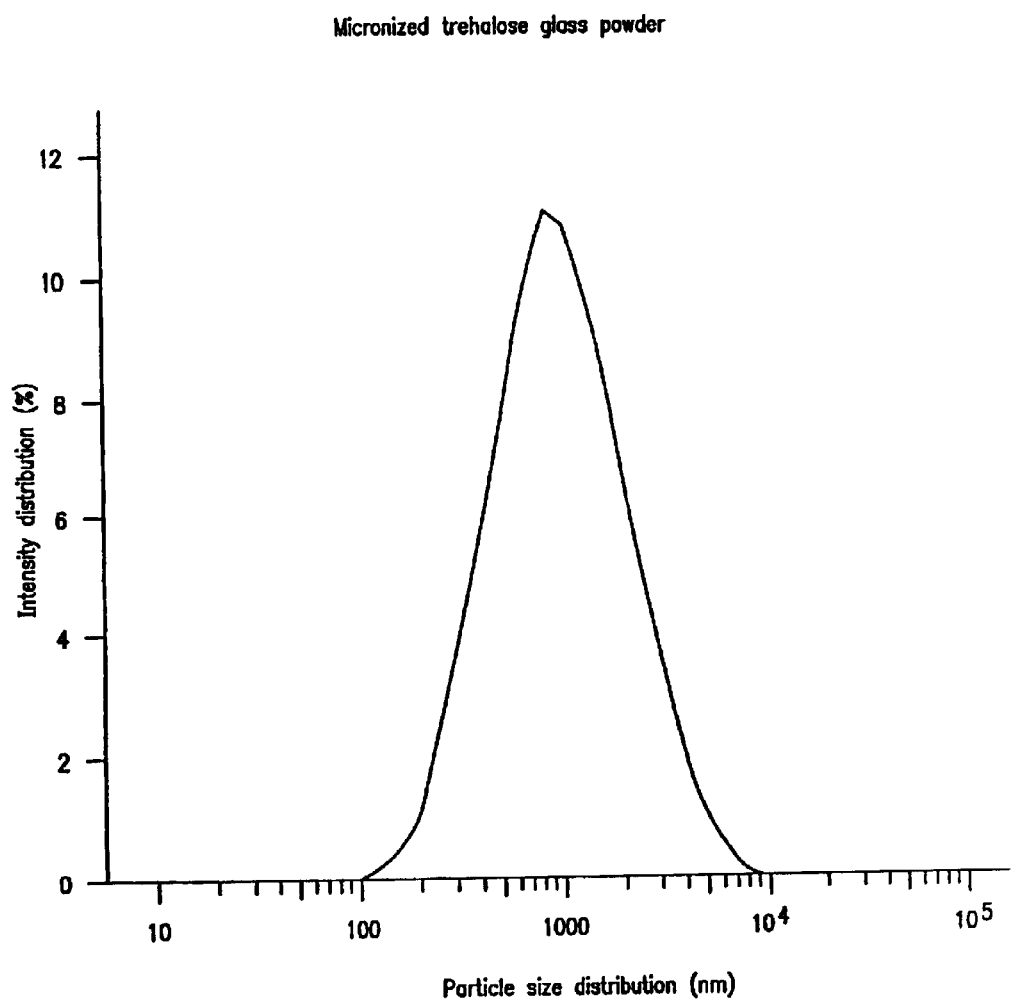
FIG. 1 is a graph depicting typical particle size distribution of micronized trehalose glass powder suitable for administration by inhalation.

The present invention comprises a solid dose delivery vehicle for mucosal, oral, topical, subcutaneous and intradermal and by-inhalation administration comprising a stabilizing polyol and a therapeutically effective amount of a bioactive material. By "solid dose" as used herein, is meant that a bioactive material delivered by the vehicle is in solid rather than liquid or aqueous form. It has now been found that stabilizing polyols can be formulated into solid vehicles suitable for drug delivery. These stabilizing polyols have been found to be particularly useful where otherwise denaturing conditions would render impossible the formulation of solid dosage forms of bioactive materials. In particular, such conditions include elevated temperatures and the presence of organic solvents.

The compositions exist as solid solutions of the bioactive material in stabilizing polyol-glass continuous phases. Previous studies have shown that in this form the product is resistant to high temperatures with the exact temperatures depending on the stabilizing polyol used. Thus, the compositions can be processed as glassy melts for brief periods without being damaged by the processing. In the same way, the stabilizing polyol containing the product would be resistant to damage during sintering with nitrate and/or carboxylate and/or derivatized carbohydrate and/or other glass-forming substances.

Examples of types of bioactive materials that may be used in the vehicle and methods of the invention include any pharmaceutical agents, including, but not limited to, antiinflammatory drugs, analgesics, antiarthritic drugs, antispasmodics, antidepressants, antipsychotics, tranquilizers, antianxiety drugs, narcotic antagonists, antiparkinsonism agents, cholinergic agonists, chemotherapeutic drugs, immunosuppressive agents, antiviral agents, antibiotic agents, appetite suppressants, antiemetics, anticholinergics, antihistaminics, antimigraine agents, coronary, cerebral or peripheral vasodilators, hormonal agents, contraceptives, antithrombotic agents, diuretics, antihypertensive agents, cardiovascular drugs, opioids, and the like.

Suitable bioactive materials also include therapeutic and prophylactic agents. These include; but are not limited to, any therapeutically effective biological modifier. Such modifiers include, but are not limited to, subcellular compositions, cells, bacteria, viruses and molecules including, but not limited to, lipids, organics, proteins and peptides (synthetic and natural), peptide mimetics, hormones (peptide, steroid and corticosteroid), D and L amino acid polymers, oligosaccharides, polysaccharides, nucleotides, oligonucleotides and nucleic acids, including DNA and RNA, protein nucleic acid hybrids, small molecules and physiologically active analogs thereof. Further, the modifiers may be derived from natural sources or made by recombinant or synthetic means and include analogs, agonists and homologs. As used herein "protein" refers also to peptides and polypeptides. Such proteins include, but are not limited to, enzymes, biopharmaceuticals, growth hormones, growth factors, insulin, monoclonal, antibodies, interferons, interleukins and cytokines. Organics include, but are not limited to, pharmaceutically active chemicals with amino, imino and guanidino groups. Suitable steroid hormones include, but are not limited to, estrogen, progesterone, testosterone and physiologically active analogs thereof. Numerous steroid hormone analogs are known in the art and include, but are not limited to, estradiol, SH-135 and tamoxifen. Many steroid hormones such as progesterone, testosterone and analogs thereof are particularly suitable for use in the present invention as they are not absorbed transdermally and, with the exception of a few analogs, are destroyed upon oral administration by the so-called hepatic first pass mechanism. Therapeutic agents prepared by the methods described herein are also encompassed by the invention. As used herein, "nucleic acids" includes any therapeutically effective nucleic acids known in the art including, but not limited to DNA, RNA and physiologically active analogs thereof. The nucleotides may encode single genes or may be any vector known in the art of recombinant DNA including, but not limited to, plasmids, retroviruses and adeno-associated viruses. Preferably, the nucleotides are administered in the powder form of the solid dose vehicle.

Compositions containing prophylactic bioactive materials and carriers therefore are further encompassed by the invention. Preferable compositions include immunogens such as vaccines. Suitable vaccines include, but are not limited to, live and attenuated viruses, nucleotide vectors encoding antigens, bacteria, antigens, antigens plus adjuvants, haptens coupled to carriers. Particularly preferred are vaccines effective against diphtheria, tetanus, pertussis, botulinum, cholera, Dengue, Hepatitis A, C and E, hemophilus influenza b, herpes virus, *Hylobacterium pylori*, influenza, Japanese encephalitis, meningococci A, B and C, measles, mumps, papilloma virus, pneumococci, polio, rubella, rotavirus, respiratory syncytial virus, Shigella, tuberculosis, yellow fever and combinations thereof. Vaccines may also be produced by molecular biology techniques to produce recombinant peptides or fusion proteins containing one or more portions of a protein derived from a pathogen. For instance, fusion proteins containing the antigen of interest and the B subunit of cholera toxin have been shown to induce an immune response to the antigen of is interest. Sanchez et al. (1989) *Proc. Natl. Acad. Sci. USA* 86:481–485.

Preferably, the immunogenic composition contains an amount of an adjuvant sufficient to enhance the immune response to the immunogen. Suitable adjuvants include, but are not limited to, aluminum salts, squalene mixtures (SAF-1), muramyl peptide, saponin derivatives, mycobacterium cell wall preparations, monophosphoryl lipid A, mycolic acid derivatives, nonionic block copolymer surfactants, Quil A, cholera toxin B subunit, polyphosphazene and derivatives, and immunostimulating complexes (ISCOMs) such as those described by Takahashi et al. (1990) *Nature* 344:873–875. For veterinary use and for production of antibodies in animals, mitogenic components of Freund's adjuvant can be used. As with all immunogenic compositions, the immunologically effective amounts of the immunogens must be determined empirically. Factors to be considered include the immunogenicity, whether or not the immunogen will be complexed with or covalently attached to an adjuvant or carrier protein or other carrier, route of administration and the number of immunizing doses to be administered. Such factors are known in the vaccine art and it is well within the skill of immunologists to make such determinations without undue experimentation.

The present invention encompasses compositions and methods of making the compositions. Although singular forms may be used, more than one polyol, more than one biological substance and more than one inhibitor of the Maillard reaction may be present. Determination of the effective amounts of these compounds is within the skill of one in the art.

As used herein, the term "carbohydrates" includes, but is not limited to, monosaccharides, disaccharides, trisaccharides, oligosaccharides and their corresponding sugar alcohols, polyhydroxy compounds such as carbohydrate derivatives and chemically modified carbohydrates, hydroxymethyl starch and sugar copolymers (Ficoll). Both natural and synthetic carbohydrates are suitable for use herein. Synthetic carbohydrates include, but are not limited to, those which have the glycosidic bond replaced by a thiol or carbon bond. Both D and L forms of the carbohydrates may be used. The carbohydrate may be non-reducing or reducing. Suitable stabilizing polyols are those in which a bioactive material can be dried and stored without losses in activity by denaturation, aggregation or other mechanisms. Prevention of losses of activity can be enhanced by the addition of various additives such as inhibitors of the Maillard reaction as described below. Addition of such inhibitors is particularly preferred in conjunction with reducing carbohydrates.

Reducing carbohydrates suitable for use in the present invention are those known in the art and include, but are not limited to, glucose, maltose, lactose, fructose, galactose, mannose, maltulose, iso-maltulose and lactulose.

Non-reducing carbohydrates include, but are not limited to, non-reducing glycosides of polyhydroxy compounds selected from sugar alcohols and other straight chain polyalcohols. Other useful carbohydrates include raffinose, stachyose, melezitose, dextran, sucrose and sugar alcohols. The sugar alcohol glycosides are preferably monoglycosides, in particular the compounds obtained by reduction of disaccharides such as lactose, maltose, lactulose and maltulose. The glycosidic group is preferably a glucoside or a galactoside and the sugar alcohol is preferably sorbitol (glucitol). Particularly preferred carbohydrates are maltitol (4-O-β-D-glucopyranosyl-D-glucitol), lactitol (4-O-β-D-galactopyranosyl-D-glucitol), iso-maltulose, palatinit (a mixture of GPS, α-D-glucopyranosyl-1→6-sorbitol and GPM), and α-D-glucopyranosyl-1→6-mannitol, and its individual sugar alcohols, components GPS and GPM.

Preferably, the stabilizing polyol is a carbohydrate that exists as a hydrate, including trehalose, lactitol and palatinit. Most preferably, the stabilizing polyol is trehalose. It has now been found that, surprisingly, solid dose compositions containing sugar hydrates like trehalose lack the "stickiness" or "tackiness" of solid dose forms containing other carbohydrates. Thus, for manufacture, packaging and administration, trehalose is the preferred carbohydrate. Trehalose, α-D-glucopyranosyl-α-D-glucopyranoside, is a naturally occurring, non-reducing disaccharide which was initially found to be associated with the prevention of desiccation damage in certain plants and animals which can dry out without damage and can revive when rehydrated. Trehalose has been shown to be useful in preventing denaturation of proteins, viruses and foodstuffs during desiccation. See U.S. Pat. Nos. 4,891,319; 5,149,653; 5,026,566; Blakeley et al. (1990) *Lancet* 336:854–855; Roser (July 1991) *Trends in Food Sci. and Tech.* 166–169; Colaco et al. (1992) *Biotechnol. Internat.,* 345–350; Roser (1991) *BioPharm.* 4:47–53; Colaco et al. (1992) *Bio/Tech.* 10:1007–1011; and Roser et al. (May 1993) *New Scientist*, pp. 25–28.

It has also now been found, surprisingly, that the glass transition temperature (Tg) of trehalose can be elevated by the addition of glass modifiers. Preferably the glass modifiers are proteins that comprise 0.002–50% of the glass modifier-trehalose mixture. Thus, the present invention encompasses the compositions and methods of making the compositions comprised of trehalose and at least one modifier, wherein the compositions have Tgs equal to or greater than the same composite glasses of pure trehalose. Suitable active glass modifiers include, but are not limited to, proteins and other hydrated macromolecules. Suitable proteins include any physiologically acceptable protein and may be inert or a protein to be delivered therapeutically, i.e. a bioactive material.

It has also been found that bioactive materials soluble only in organic solvents can be dried in trehalose from an organic/aqueous solvent to give a conformation that is now soluble in aqueous solvents. Methods of making the dried material and compositions obtained thereby are provided by the invention. The bioactive material is dissolved in an organic/aqueous solvent in combination with an effective amount of trehalose and then dried. This gives a solid solution of the bioactive material in a trehalose glass which then readily dissolves in an aqueous solution to give an aqueous suspension of the insoluble bioactive material. It has now been shown that the immunosuppressant cyclosporin A (which is insoluble in water and normally administered as an oil emulsion) in a solution of trehalose in a 1:1 ethanol:water mixture can be dried to give a clear glass of trehalose containing cyclosporin A. This glass can be milled to give a free flowing powder which if added to water dissolves instantaneously to give a suspension of cyclosporin A in water. If the solution dried contained a mixture of trehalose/trehalose octaacetate (insoluble in water), then the glass formed can be tailored for different dissolution rates by varying the ratio of the two.

Preferably, the compositions contain an amount of at least one physiologically acceptable salt which effects a loss of water from the composition so that at ambient humidity the vapor pressure of water of crystallization is at least 14 mm Hg (2000 Pa) at 20° C. (molecular water-pump buffer, hereinafter referred to as "MWPB") and does not interfere with glass formation of the stabilizing polyol. In the case of powders for pulmonary administration, addition of an effective amount of MWPBs is particularly preferred as they have been found to prevent wetting and clumping. An effective amount of an MWPB is one which substantially prevents wetting and clumping. Suitable salts are those described in Spanish pat. no. 2009704. These may constitute a buffer system or may replace a substantial amount of a component of the buffer in a conventional formulation. Suitable salts include, but are not limited to, ammonium chloride, orthophosphate and sulfate; barium chloride dihydrate; calcium lactate pentahydrate; copper sulfate pentahydrate; magnesium salicylate tetrahydrate, magnesium sulfate heptahydrate; potassium bisulfate, bromide, chromate and dihydrogen orthophosphate; sodium acetate trihydrate, bromoiridate dodecahydrate, carbonate decahydrate, fluoride, hydrogen orthophosphate dodecahydrate, metaperiodate trihydrate, metaphosphate trihydrate and hexahydrate, sulfite heptahydrate, sulfate heptahydrate and decahydrate and thiosulfate pentahydrate; and zinc sulfate heptahydrate and combinations thereof.

Preferably, if the bioactive material and/or glass forming polyol contain carboxyl and amino, imino or guanidino groups, the compositions further contain at least one physiologically acceptable inhibitor of the Maillard reaction in an amount effective to substantially prevent condensation of amino groups and reactive carbonyl groups in the composition.

The inhibitor of the Maillard reaction can be any known in the art. The inhibitor is present in an amount sufficient to prevent, or substantially prevent, condensation of amino groups and reactive carbonyl groups. Typically, the amino groups are present on the bioactive material and the carbonyl groups are present on the carbohydrate, or the converse. However, the amino and carbonyl groups may be intramolecular within either the biological substance or the carbohydrate. Various classes of compounds are known to exhibit an inhibiting effect on the Maillard reaction and hence to be of use in the compositions described herein. These compounds are generally either competitive or noncompetitive inhibitors. Competitive inhibitors include, but are not limited to, amino acid residues (both D and L), combinations of amino acid residues and peptides. Particularly preferred are lysine, arginine, histidine and tryptophan. Lysine and arginine are the most effective. There are many known noncompetitive inhibitors. These include, but are not limited to, aminoguanidine and derivatives and amphotericin B. EP-A-O 433 679 also describes suitable Maillard inhibitors which are 4-hydroxy-5,8-dioxoquinoline derivatives.

As discussed below, the composition may further contain at least one physiologically acceptable glass. Suitable glasses include, but are not limited to, carboxylate, nitrate, sulfate, bisulfate, carbohydrate derivatives and combinations thereof. Carboxylate and carbohydrate derivatives are preferred where water soluble glasses are required as many of these derivatives are slowly soluble in water. Suitable glasses include, but are not limited to, those described in PCT/GB 90/00497.

The composition may also be coated with one or more layers of a phosphate glass having a predetermined solution rate. The composition may further contain other water soluble and biodegradable glass formers. Suitable glass formers include, but are not limited to, lactide and lactide/glycolide copolymers, glucuronide polymers and other polyesters, polyorthoesters, and polyanhydrides.

In one embodiment, the delivery vehicle of the invention is sized and shaped for penetration of the epidermis and is suitable for ballistic delivery. Suitable vehicle size is thus on the order of microns, preferably in the range of 1–5 microns in diameter and 5–150 microns in length, which allows penetration and delivery through the epidermis to subcutaneous and intradermal tissues. It will be appreciated that, at this size, the delivery vehicle may macroscopically appear to be in powder form, regardless of its configuration at the microscopic level.

Preferred configurations of the delivery vehicle of the invention are microneedles and microfibers of a stabilizing polyol glass. The manufacture of microfibers is relatively simple and economical and results in stable delivery vehicles comprised of the stabilizing polyol and the bioactive material. Additional stabilizers, buffers, glasses and polymers may also be added as described herein. Many of the most labile biomolecules can withstand high temperatures (e.g., 60–100° C.) when stabilized by drying in trehalose, provided that the majority of their surface is in contact with the stabilizing polyol. Temperatures of 70° C. can be tolerated for over a month (Colaco et al. (1992) Bio/Technology 10:1007–1011) and higher temperatures for shorter periods. The results presented herein show that the fluorescent protein phycoerythrin dried in trehalose can be stored at 100° C. for at least one month with no detectable loss of functional activity. Other stabilizing polyols give protection at lower temperatures than trehalose. The maximum temperature of protection must be determined empirically and is within the skill of one in the art without undue experimentation.

Providing the exposure time is limited, bioactive materials admixed in dry stabilizing polyols can be heated to fluidize the glass which can then be drawn or spun as a fiber without damage to the product. Fibers can either be drawn from a billet and wound onto a drum or they can be spun through fine holes in a rapidly rotating cylinder that is heated above the melting point of the glass. Being inherently brittle, these glass fibers can be readily crushed or chopped into short lengths to form long cylindrical rods or needles. By varying the diameter of the fibers produced, needles can be formed which vary from micro to macro needles, i.e., from thicknesses of a few microns to fractions of a millimeter. It has been found that cotton candy machines are suitable for use in preparing the microfibers. Although the optimal conditions must be determined empirically for each stabilizing polyol, such determinations are well within the skill of one in the art.

The microfibers prepared in accord with the principles of the present invention, have a relatively high aspect ratio, i.e., length compared to diameter, preferably in the range of 1–5 microns in diameter and 5–150 microns in length. This high aspect ratio provides for enhanced "end on" penetration upon ballistic delivery, by the tendency of the microfibers to lineup parallel to the barrel of the ballistic microinjector, described in more detail below. Longer macrofibers may be injected using conventional impact ballistic devices or by trocar.

Alternative preferred embodiments of the delivery vehicle include uniform microspheres, preferably with a narrow size distribution. This configuration is particularly useful when increased control of the depth of penetration of the delivery vehicle is desirable. Such control would be useful, for example, for intradermal delivery of vaccines to the basal layer of the epidermis, to bring antigen into proximity to the Langerhans cells of the skin to induce optimal immune responses.

To prepare microspheres of the present invention, several methods can be employed depending upon the desired application of the delivery vehicles. Suitable methods include, but are not limited to, spray drying, freeze drying, air drying, vacuum drying, fluidized-bed drying, milling, co-precipitation and critical fluid extraction. In the case of spray drying, freeze drying, air drying, vacuum drying, fluidized-bed drying and critical fluid extraction; the components (stabilizing polyol, bioactive material, buffers etc.) are first dissolved or suspended in aqueous conditions. In the case of milling, the components are mixed in the dried form and milled by any method known in the art. In the case of co-precipitation, the components are mixed in organic conditions and processed as described below. Spray drying can be used to load the stabilizing polyol with the bioactive material. The components are mixed under aqueous conditions and dried using precision nozzles to produce extremely uniform droplets in a drying chamber. Suitable spray drying machines include, but are not limited to, Buchi, NIRO, APV and Lab-plant spray driers used according to the manufacturer's instructions. A number of carbohydrates are unsuitable for use in spray drying as the melting points of the carbohydrates are too low causing the dried materials to adhere to the sides of the drying chamber. Generally, carbohydrates with a melting point of less than the spray drying chamber are unsuitable for use in spray drying. For example, palatinit and lactitol are not suitable for use in spray drying under conventional conditions. A determination of suitable carbohydrates can thus be made on known melting points or determined empirically. Such determinations are within the skill of one in the art.

An alternative method for manufacturing microspheres as delivery vehicles in accord with the present invention is to prepare a uniform aqueous/organic phase emulsion of the bioactive material in a solution of the stabilizing polyol as the aqueous phase and the glass former in the organic phase. This is followed by drying of the emulsion droplets to form a solid solution of the bioactive material and stabilizing polyol in an amorphous matrix of the glass former. In a modification of this method, the emulsion may be formed from the bioactive compound in solid solution in the stabilizing polyol and two different polymers dissolved together in one solvent, or dissolved into two separate solvents. The solvent(s) are then removed by evaporation to yield double or multi-walled microspheres. Suitable methods for making multi-walled microspheres are described, for instance, in Pekarek et al. (1994) Nature 367:258–260; and U.S. Pat. No. 4,861,627.

The bioactive material can also be dried from an organic solution of the stabilizing polyol and the bioactive material to form a glass containing homogeneously distributed bioactive material in solid solution in the polyol glass. These glasses can then be milled and/or micronized to give microparticles of homogeneous defined sized.

The bioactive material and the stabilizing polyol can also be co-precipitated to give high quality powders. Co-precipitation is performed by spraying, for instance with an air brush, the bioactive material and stabilizing polyol and/or glass former into a liquid in which neither dissolves, such as ice-cold acetone.

The invention also encompasses hollow fibers for delivery of bioactive materials. By drawing down a heated hollow billet, fine hollow needles can be formed. These can be made to contain a finely powdered stabilized compound by introduction of the fine powder during the melting and drawing down process. The hollow fiber can also be made of thermoplastic, organic polymer and/or carbohydrate and/or derivatized carbohydrate glass which may itself be water soluble or biodegradable.

An alternative embodiment of the delivery vehicle in the invention comprises a hollow vehicle comprised of water soluble glass or plastic which is filled and optionally coated with stabilizing polyol glass and the bioactive material. Fine hollow fibers of water-soluble inorganic or organic glasses can be drawn from a hollow billet and a finely powdered stabilizing polyol-bioactive material can be incorporated into the lumen of the billet, and therefore of the fiber, during the process. Alternatively, hollow needles of these glasses may be filled by allowing capillarity to draw up suspensions of the finely powdered bioactive substance in a volatile organic solvent which is subsequently removed by evaporation leaving the needle filled with the bioactive substance. In a modification of this method, incorporation of a soluble glass former in the organic solvent phase will result in the needle being filled with the bioactive substance in solid solution in the glass former.

In another embodiment of the invention, coformulations of stabilizing polyol glass and other water soluble materials are included. For example, coformulations of stabilizing polyol glass with water-soluble glasses such as phosphate glasses (Pilkington Glass Company) or biodegradable plastics such as lactide or lactide/glycolide copolymers will yield a more slowly eroding vehicle for delayed release of the bioactive material. A finely powdered stabilizing polyol glass/bioactive material can be intimately mixed with a finely powdered carboxylate glass and co-sintered. Alternatively, if a metal carboxylate glass has a lower melting point than the stabilized bioactive polyol glass, the latter can be homogeneously embedded as a solution in a carboxylate glass by cooling the melt obtained. This can be milled to give a fine powder with solubilities intermediate between the rapid solubility of the stabilizing polyol and the slow solubility of the carboxylate glass.

Alternate coformulations include the use of a homogeneous suspension of the finely powdered bioactive material/ stabilizing polyol mixture encapsulated in a carboxylate glass by drying from an organic solution of the carboxylate to form the carboxylate glass. This can be ground to give a fine powder which would have the rapidly dissolving stabilizing polyol glass containing the encapsulated bioactive material entrapped within a slow dissolving carboxylate glass (i.e., a conventional slow-release system). Pulsatile release formats can be achieved either by repeated encapsulation cycles using glasses of different dissolution rates, or by mixing powders of a number of coformulations with the desired range of release characteristics. Note that this glass could also be drawn or spun to give microfibers or microneedles which would be slow-release implants. It will be appreciated that any stabilizing polyol formulation should be such that it is capable of releasing the bioactive material upon administration, and should not unduly effect the stability of the material being administered.

As discussed above, glasses of derivatized carbohydrates are also suitable for use herein. Suitable derivatized carbohydrates include, but are not limited to, carbohydrate esters, ethers, imides and other poorly water-soluble derivatives and polymers.

The delivery vehicle is loaded with the bioactive materials to be delivered to the tissue by drying a solution of the bioactive material containing a sufficient quantity of stabilizing polyol to form a glass on drying. This drying can be accomplished by any method known in the art, including, but not limited to, freeze drying, vacuum, spray, belt, air or fluidized-bed drying. The dried material can be milled to a fine powder before further processing the material with the polyol glass or coformulation.

Different dosing schemes can also be achieved depending on the delivery vehicle employed. A stabilizing polyol glass delivery vehicle of the invention can provide for a quick release or flooding dose of the bioactive material after administration, upon the dissolving and release of the bioactive material from the stabilizing polyol glass. Coformulations of stabilizing polyol with water soluble glasses and plastics such as phosphate, nitrate or carboxylate glasses and lactide/glycolide, glucuronide or polyhydroxybutyrate plastics and polyesters, can provide more slowly dissolving vehicles for a slower release and prolonged dosing effect. A booster effect can also be realized by utilizing a hollow water soluble vehicle filled and coated with a stabilizing polyol glass loaded with the bioactive material. The polyol glass coating loaded with the material will dissolve rapidly to give an initial dosing effect. While the hollow outer portion of the vehicle dissolves, there will be no dosing action, followed by a booster effect of the inner filling comprised of a stabilizing polyol and a bioactive material when the hollow outer portion is breached by dissolution. Such pulsatile release format is particularly useful for vaccine delivery. Should multiple effect pulsatile delivery be desirable, delivery vehicles with any combination of layers of water soluble "non-loaded" materials and stabilizing polyol glass loaded with the bioactive material can be constructed.

The delivery of more than one bioactive material can also be achieved using a delivery vehicle comprised of multiple coatings or layers of the stabilizing polyol loaded with different materials or mixtures thereof. Administration of the solid dose delivery vehicle of the present invention can be used in conjunction with other conventional therapies and coadministered with other therapeutic, prophylactic or diagnostic substances.

The invention further encompasses methods of delivery. Suitable delivery methods include, but are not limited to, topical, transdermal, transmucosal, oral, gastrointestinal, subcutaneous, ocular, and by-inhalation (naso-pharyngeal and pulmonary, including transbronchial and transalveolar). Topical administration is, for instance, by a dressing or bandage having dispersed therein the stabilizing polyol glass/bioactive material, or by direct administration into incisions or open wounds. Creams or ointments having dispersed therein slow release beads of bioactive material/stabilizing polyol are suitable for use as topical ointments or wound filling agents.

Compositions for transdermal administration are preferably powders of microneedles or microbeads. Larger, macroscopic needles and beads are also provided for subdermal implantation and extended drug delivery. The particle sizes should be small enough so that they do not cause skin damage upon administration. Preferably, the powders are microneedles of approximately 10–1,000 microns in length and 1–150 microns in diameter. The powders may be prepackaged in single-dose, sealed, sterile formats. Suitable methods of transdermal administration include, but are not limited to, ballistic, trocar and liquid jet delivery. Ballistic administration is preferred as it is relatively painless. Generally the delivery vehicle is accelerated in a shock wave of helium or another gas and fired into the epidermis. A suitable device for ballistic delivery is described in PCT/GB 94/00753. A suitable device for liquid-jet delivery is a Medi-ject device (Diabetes Care (1993) 1b, 1479–1484). Such liquid-jet devices are particularly useful with the larger macroneedle delivery vehicles which may also be delivered by the use of conventional impact ballistic devices or by trocar.

Upon transdermal administration, the degree of penetration of the delivery vehicle can be controlled to a certain degree, not only by the ballistic microinjector, described below, but also the shape and size of the powder particles. For example, when a relatively uniform and lesser degree of penetration is desirable, microspheres may be more suitable for the practice of the present invention. When a greater degree of penetration is desirable, a microfiber configuration may be preferred. Because the aspect ratio (i.e., length to diameter) of the microneedles is high they have higher masses than spherical particles with a similar diameter. If they can be induced to impact with the skin "end-on," their higher mass will give them a higher momentum for the same velocity and they will thus penetrate deeper into the tissues. When randomly orientated microneedles are put into a laminar flow of gas, they will align themselves in the direction of the air flow and in the gas-propelled ballistic injector this will ensure that they impact the skin at the right angles and thus penetrate it.

The compositions suitable for transmucosal delivery include, but are not limited to, lozenges for oral delivery, pessaries, and rings and other devices for vaginal or cervical delivery.

Compositions suitable for gastrointestinal administration include, but are not limited to, pharmaceutically acceptable powders and pills for ingestion and suppositories for rectal administration.

Compositions suitable for subcutaneous administration include, but are not limited to, various implants. Preferably the implants are macroscopic spherical or cylindrical shapes for ease of insertion and may be either fast or slow release. Since the entire implant is dissolved in the body fluids, removal of the implant is not necessary. Furthermore, the implants do not contain synthetic polymers and thus are less likely to initiate a separate immune response.

Compositions suitable for ocular administration include, but are not limited to microsphere and macrosphere formulations, and saline drops.

Compositions suitable for by-inhalation administration include, but are not limited to, powders of bioactive material/stabilizing polyol. Preferably the powders are of a particle size 0.1 to 10 microns. More preferably, the particle size is 0.5 to 5 microns. Most preferably, particle size is 1 to 4 microns. In particular for pulmonary administration, the preferred particle size is 2.5–3 microns. Preferably the powders also contain an effective amount of a physiologically acceptable MWPB. An effective amount of an MWPB is one which sufficiently reduces wetting to prevent substantial clumping, for instance, a 50% molar ratio of potassium sulfate. Sodium sulfate and calcium lactate are the preferred salts with potassium sulfate being the most preferred. Atomizers and vaporizers filled with the powders are also encompassed by the invention.

There are a variety of devices suitable for use in by-inhalation delivery of powders. See, e.g., Lindberg (1993) *Summary of Lecture at Management Forum* Dec. 6–7, 1993 "Creating the Future for Portable Inhalers." Additional devices suitable for use herein include, but are not limited to, those described in WO9413271, WO9408552, WO9309832 and U.S. Pat. No. 5,239,993.

The following examples are provided to illustrate but not limit the present invention.

EXAMPLE 1

Methods of Making Solid Dose Delivery Vehicles a) Carbohydrate Class Microfiber Formation.

Glasses were formed by drying 20% solutions of either trehalose, lactitol, palatinit or GPS, containing MWPB and 1 mg/ml of the fluorescent algal protein phycoerythrin under vacuum (80 mTorr) for 16 hrs. The glasses were ground in a domestic coffee mill to yield a coarse powder which was used to fill the spinning head of a Kando K1 Kandy Floss cotton candy machine (GB Patent No. 00103/76). The motor was then switched on and the powdered sugar glass heated at element settings between 5 and 9. Residence time in the spinning head was 2–10 min and a continuous process was maintained by constantly topping up the head.

The fibers produced were ground in a domestic coffee grinder and the results obtained are presented in Table 1, which shows an average of the needles produced. These data indicate that, with all three sugar glasses, reduced element settings result in the production of finer diameter microneedles. With trehalose, setting 6 gave microneedles with a mean diameter of 15 microns, and setting 9, microneedles with a mean diameter of 40 microns. With GPS, setting 9 gave microneedles with a mean diameter of 15 microns. Microneedles formed from glasses containing buffer salts remained dry at ambient temperatures and humidities.

Microneedles containing phycoerythrin showed retention of biological activity as assessed by fluorescence.

TABLE 1

| Microneedle size analysis | Length ($\mu$m) | Width ($\mu$m) |
|---|---|---|
| Mean | 192.60 | 43.35 |
| Standard Error | 12.53 | 2.33 |
| Median | 167.5 | 37.5 |
| Mode | 137.5 | 47.5 |
| Standard Deviation | 123.44 | 22.91 |
| Sample Variance | 15237.75 | 524.72 |
| Kurtosis | 16.17 | 2.55 |
| Skewness | 3.35 | 1.45 |
| Range | 862.5 | 115 |
| Minimum | 67.5 | 10 |
| Maximum | 930 | 125 |
| Sum | 18682.5 | 4205 |
| Count | 97 | 97 |
| Confidence Level (95.000%) | 24.57 | 4.56 | b) Binary Carbohydrate/Organic Mixture Glass Microfiber Formation.

Glasses were formed by drying a 5:1:1 mixture of trehalose, sodium octanoate and water under vacuum (80 mTorr) for 16 hrs. The glasses were ground in a domestic coffee mill to yield a coarse powder which was used to fill the spinning head of a Kando K1 Kandy Floss machine. The motor was then switched on and the powdered binary carbohydrate/organic glass heated at element settings between 5 and 9. As with pure trehalose glasses, reduced element settings resulted in the production of finer diameter microneedles. The binary mixture glasses can be tailored to yield glasses with significantly different tensile properties compared to the corresponding pure trehalose glasses. Residence time in the spinning head was again 2–10 min and a continuous process was maintained by constantly topping up the head. The results obtained indicate that variations of the melting points and dissolution times of the glasses and the resulting physical properties of the microfibers can be achieved by varying both the carbohydrate/organic molecules and ratios used.

EXAMPLE 2

Methods of Making Solid Dose Delivery Vehicles a) Micronized Powder Preparation.

Figure 2A:
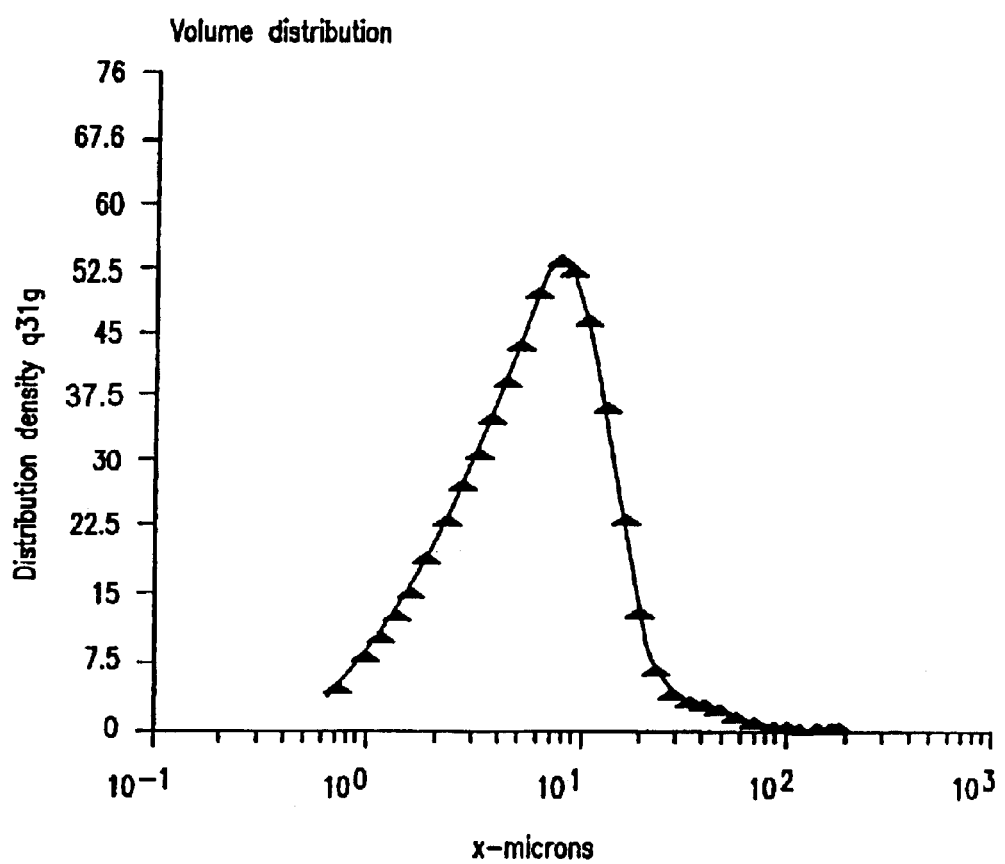
FIG. 2A is a graph depicting the sharp particle size distribution for trehalose/MWPB glass powder.
Figure 2B:
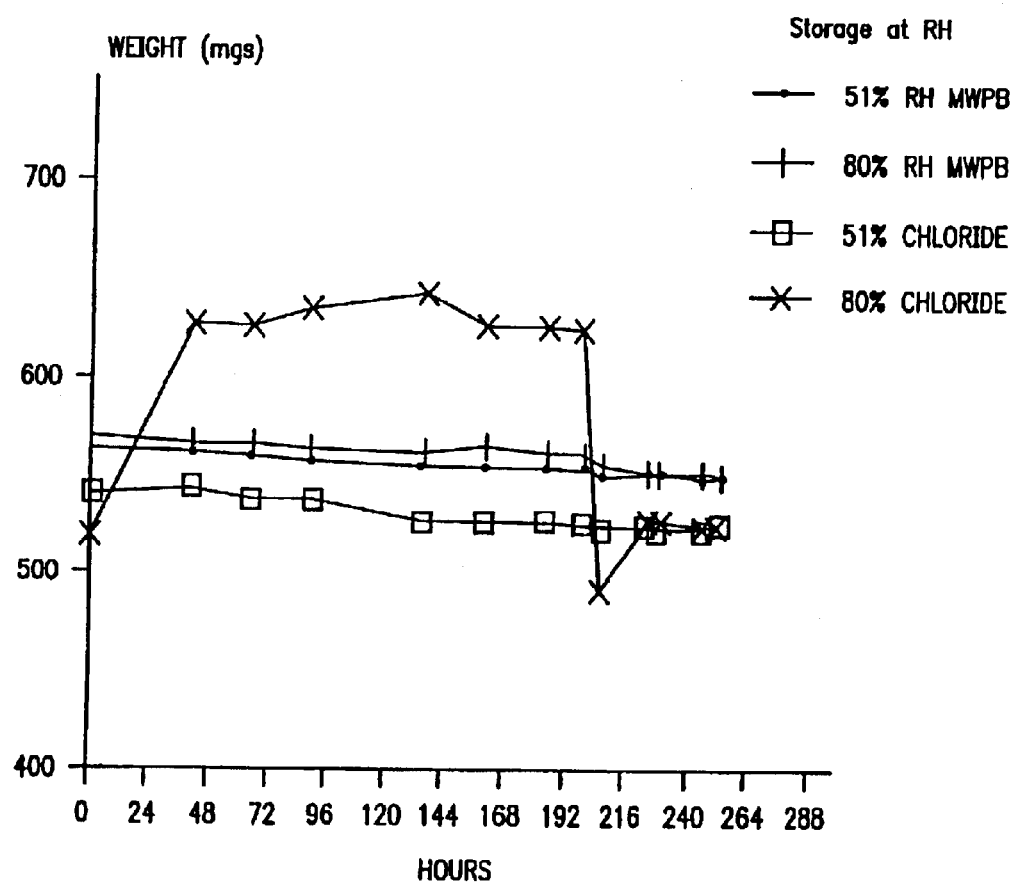
FIG. 2B is a graph depicting the wetting of various trehalose/MWPB glass powders after storage at ambient temperature and relative humidities.

Glasses were formed by drying 20% solutions of either trehalose, lactitol, palatinit, GPM or GPS, containing an equimolar ratio of MWPB and protein, by freeze-drying under vacuum (80 mTorr) for 16 hrs. The glasses were powdered using a Trost air-jet mill. Particle size in the micronized powders were measured using a Malvern Mastersizer laser particle sizer. The results obtained with micronized powders obtained from an original solution of 0.5 M trehalose and 0.5 M calcium lactate showed a monodisperse particle distribution with mean particle diameters of 1.1 microns (FIG. 1). The powders containing MWPB remained a free-flowing powder and showed no change in particle size or clumping and uptake of water on extended exposure to ambient temperatures and humidities (FIGS. 2A and 2B).

b) Spray-Dried Powder Preparation.

Figure 4:
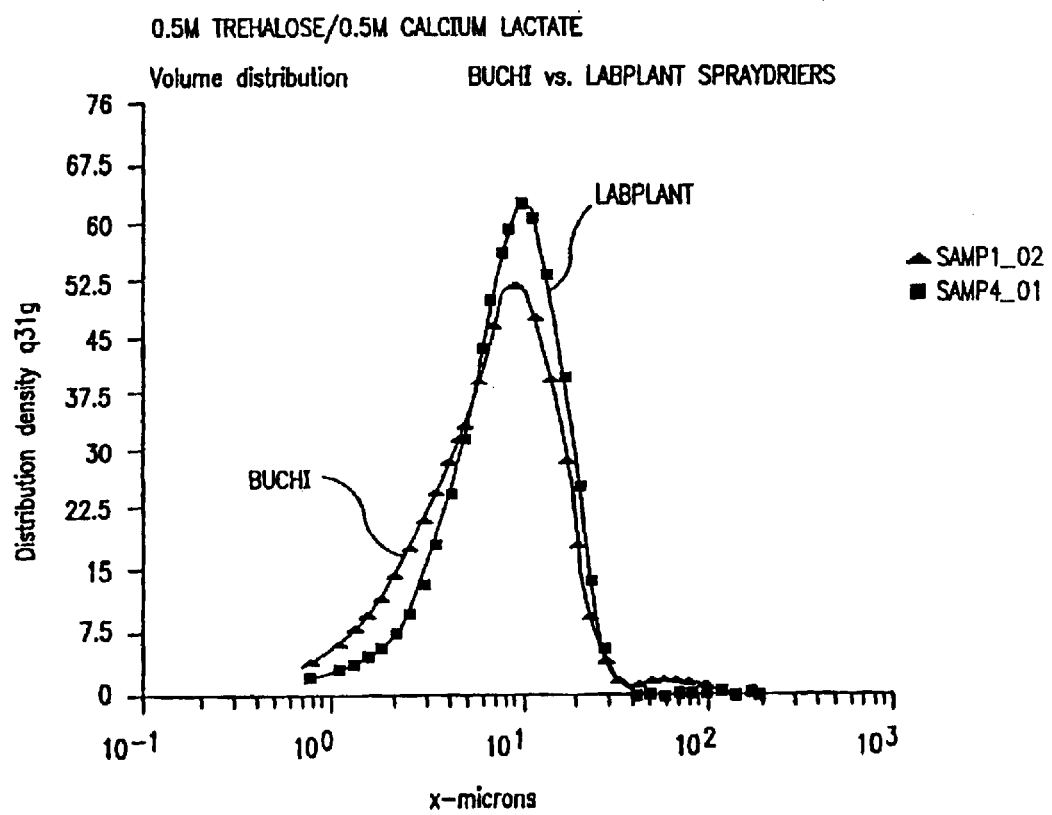
FIG. 4 is a graph depicting a comparison of the sharp particle size distribution for trehalose glass powders prepared with two different spray-dryers (Lab-plant and Buchi, as indicated).

20% solutions of trehalose containing MWPB salts and protein (phycoerythrin) were dried in a Buchi or Lab-Plant spray drier at a pump speed of 500–550 ml/hr and an inlet temperature of 180° C. Particle size was again measured using a SympaTec laser particle sizer. The spray-dried powders showed a monodisperse particle distribution with a sufficiently narrow peak size distribution for effective use as particles in a powder ballistic device. In the results shown in FIG. 3, particle size analysis of a spray-dried powder produced by spray drying a mixture of 0.5 M trehalose and 0.5 M calcium lactate on a Lab-Plant spray drier showed a mean particle diameter of 8.55 microns and illustrates the tight peak distribution obtained. Variation of the mean particle size can be achieved by varying either the composition of the mixture to be spray dried or the characteristics of the spray drier nozzle assembly used. The results shown in FIG. 4 provide a comparison of the particle size analysis of the spray-dried powder as in FIG. 3 with a spray-dried powder produced by drying the same mixture on the Buchi spray drier which uses a different nozzle assembly. The peak distribution shown in FIG. 4 shows an equally narrow range but the mean particle size is now 7.55 microns. These data show that the particles obtained by different spray-drying processes are equally suitable to provide compositions for ballistic delivery. Note that the ability to vary particle size results in compositions with different penetrative characteristics. This is particularly important for determining intradermal or intramuscular delivery as the penetration is a function of particle momentum and the distribution is a function of the scatter of particle size.

c) Drying from Organic Solvents

A 50 mg/ml solution of cyclosporin A in a 1.1 mixture of ethanol:water, containing 20% trehalose, was air-dried at ambient temperature to form a clear trehalose glass containing cyclosporin A in solid solution. The glass was ground to give a powder, according to the method described in Example 1, and remained a free-flowing powder at ambient temperature and humidities. Addition of the powder to water resulted in the dissolution of the trehalose and the formation of a uniform aqueous suspension of cyclosporin A.

d) Co-Precipitation Powder Preparation

20% solutions of trehalose, lactitol, palatinit, GPM or GPS, containing MWPB and protein (phycoerythrin) were dried by spraying into an acetone-solid carbon dioxide freezing bath. The precipitated powders were separated by centrifugation or filtration and air dried to remove residual solvent. The powders again showed a monodisperse particle distribution and those containing buffer formulation salts remained dry at ambient temperatures and humidities.

EXAMPLE 3

Variable Solubility of Glasses of Carbohydrate/Carbohydrate Ester Coformulations Various ratios of trehalose and trehalose octaacetate (TOAC) or two different carbohydrate esters were dissolved in pyridine with sufficient water added to give a clear solution. The solutions were dried rapidly to give clear transparent monophasic glasses of the carbohydrate and/or carbohydrate ester mixes. TOAC is almost insoluble in water and increased amounts of the ester in the mixture resulted in the increased dissolution times of the coformulated glass formed.

Figure 5:
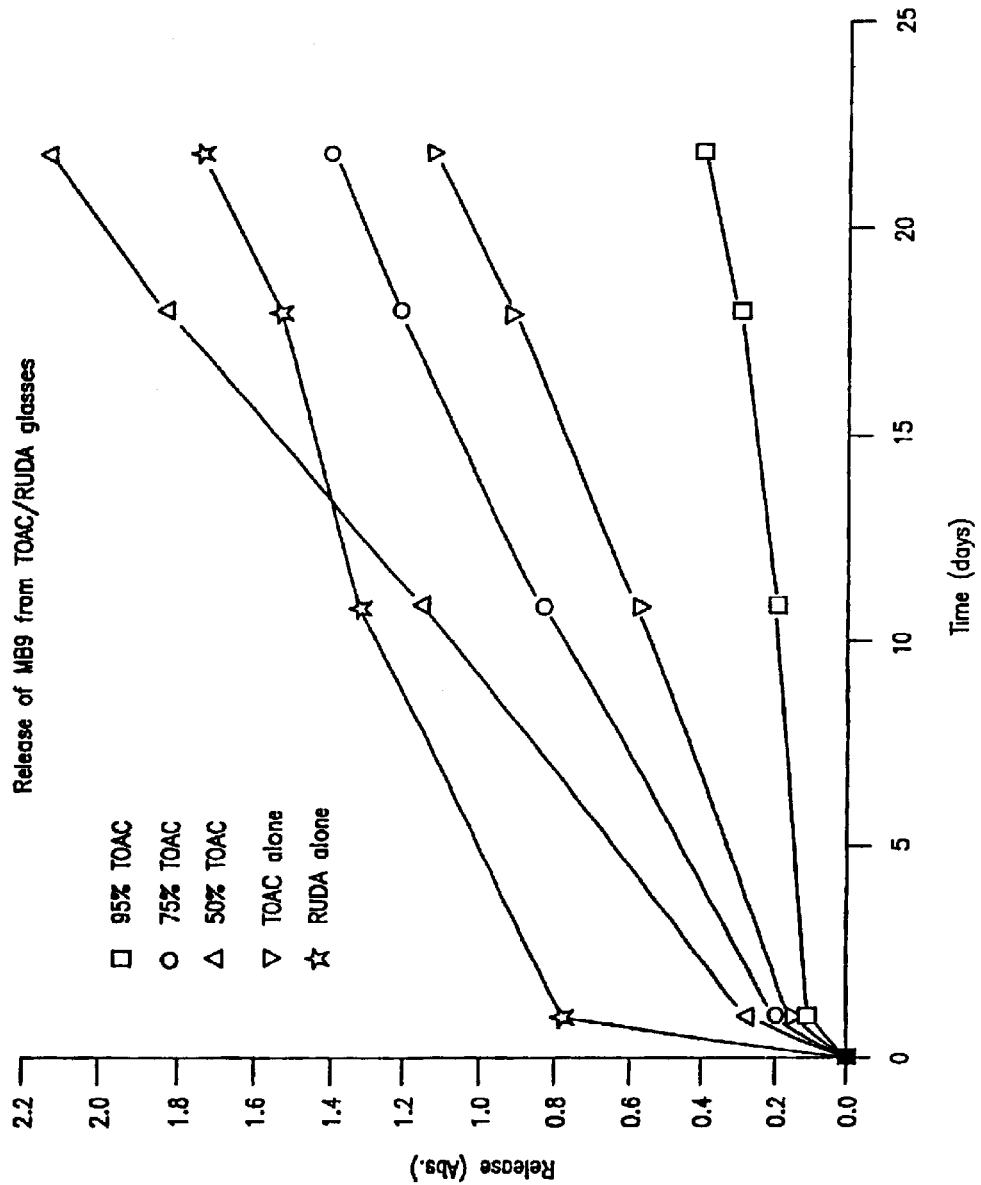
FIG. 5 is a graph depicting the release of a dye (Mordant Blue 9) from coformulated melt glasses of trehalose octaacetate (TOAC) and raffinose undecaacetate (RUDA).

Coformulations of TOAC and raffinose undecaacetate containing 1–2% Mordant Blue (MB9) dye were prepared as described above. The release rates of MB9 were measured by absorbance quantitated spectrophoto-metrically and the results are depicted in FIG. 5. These results indicate that glasses of two carbohydrate derivatives provide different release characteristics and that the use of two or more carbohydrate derivatives results in glasses tailored to provide desired release characteristics.

EXAMPLE 4

Figure 6A:
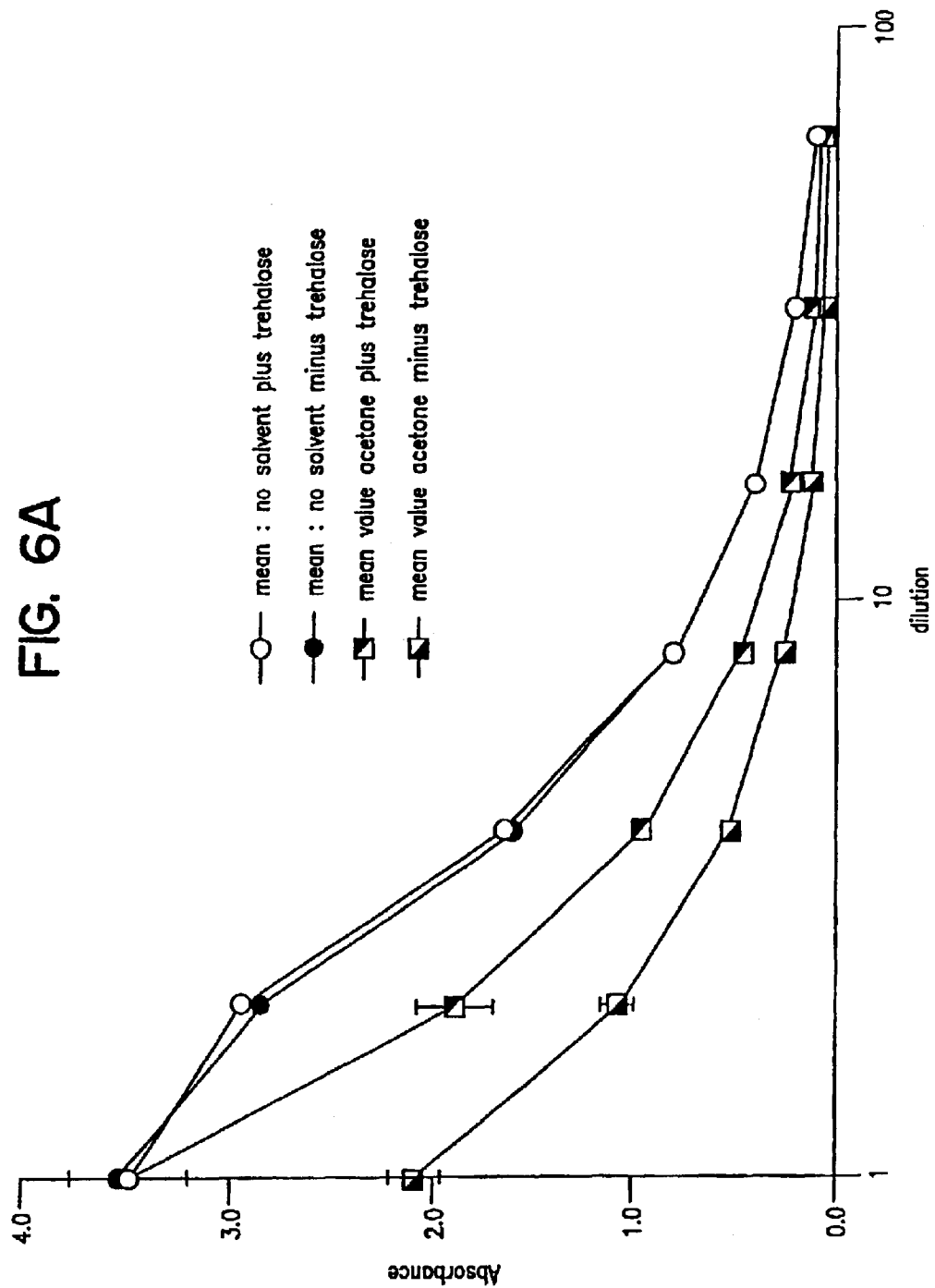
FIG. 6A is a graph depicting the resistance of horseradish peroxidase to acetone effected by drying the enzyme with trehalose.
Figure 6B:
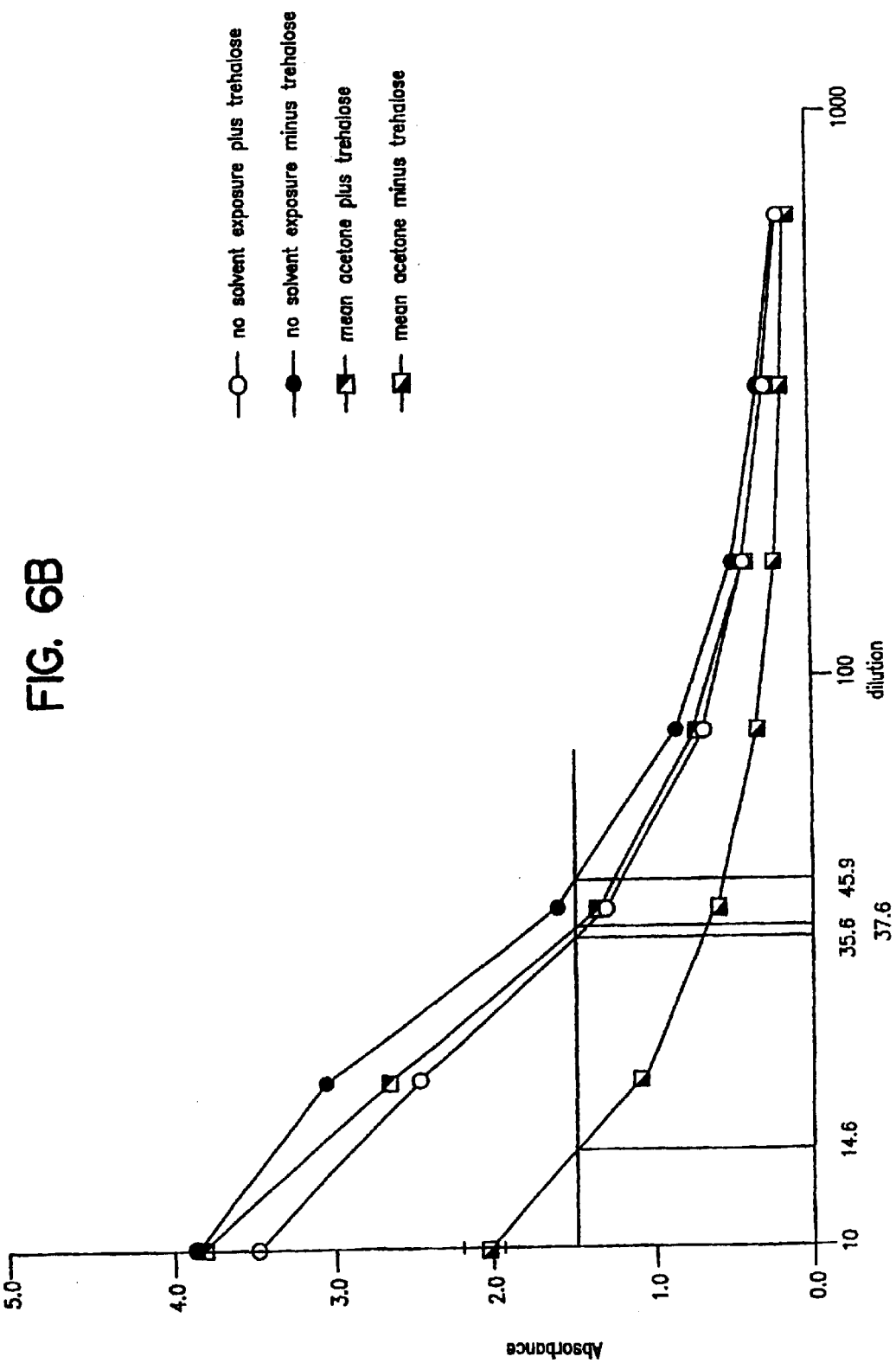
FIG. 6B is a graph depicting the resistance of alkaline phosphatase to acetone effected by drying the enzyme with trehalose.

Protection of Proteins Against an Organic Solvent and Elevated Temperatures Effected by Drying in Trehalose a) Protection of Horseradish Peroxidase and Alkaline Phosphatase Against Acetone Effected by Drying in Trehalose A 0.1 mg/ml horseradish peroxidase solution or a 1 mg/ml alkaline phosphatase/4 mg/ml bovine serum albumin solution was dried in an FTS Systems freeze drier with or without 50% trehalose. The drier was used as a vacuum drier and the mixtures dried without freezing. Four times the volume of solvent was added and the solution was allowed to evaporate to dryness. The contents were redissolved in 5 milliliters of water, and enzyme activity was assessed, in serial dilution, by commercial 'kit' reagents. The alkaline phosphatase kit was obtained from Sigma Chemical Co. and the horseradish peroxidase kit was obtained from Kirkegaard & Perry Laboratories, Inc. As shown in FIGS. 6A and 6B, the enzymes dried with trehalose were more resistant to acetone than the enzymes dried without trehalose.

b) Protection of Phycoerythrin Against Organic Solvents Afforded by Drying in Trehalose A 400 µg/ml phycoerythrin solution was freeze-dried in a Labconco freeze-drier with or without 20% trehalose. The dried protein powder was exposed to a number of organic solvents for 72 hrs. The phycoerythrin remained fluorescent in acetone, acetonitrile chloroform and methanol. In pyridine, the phycoerythrin remained fluorescent for 24–48 hr but began wetting and lost fluorescence by 72 hrs. In dimethylsulfoxide, the powder solubilized but the phycoerythrin remained fluorescent.

c) Protection of Phycoerythrin Against 100° C. Afforded by Drying in Trehalose

A 400 µg/ml phycoerythrin solution was freeze-dried in the FTS drier with or without 20% trehalose. The dried protein was stored at 100° for one month with no loss of functional activity.

d) Effect of Protein on Tg of Trehalose

Figure 7:
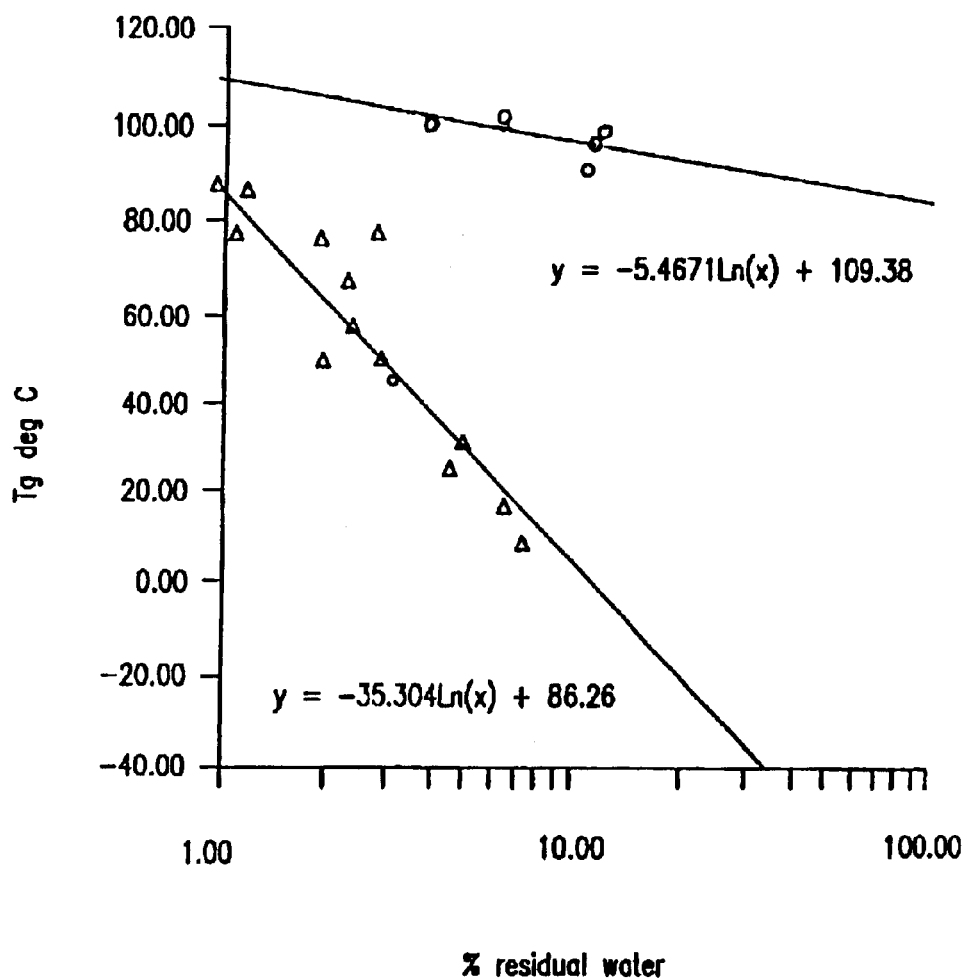
FIG. 7 is a graph depicting the effect of a glass modifier on the Tg of Trehalose.
Figure 8:
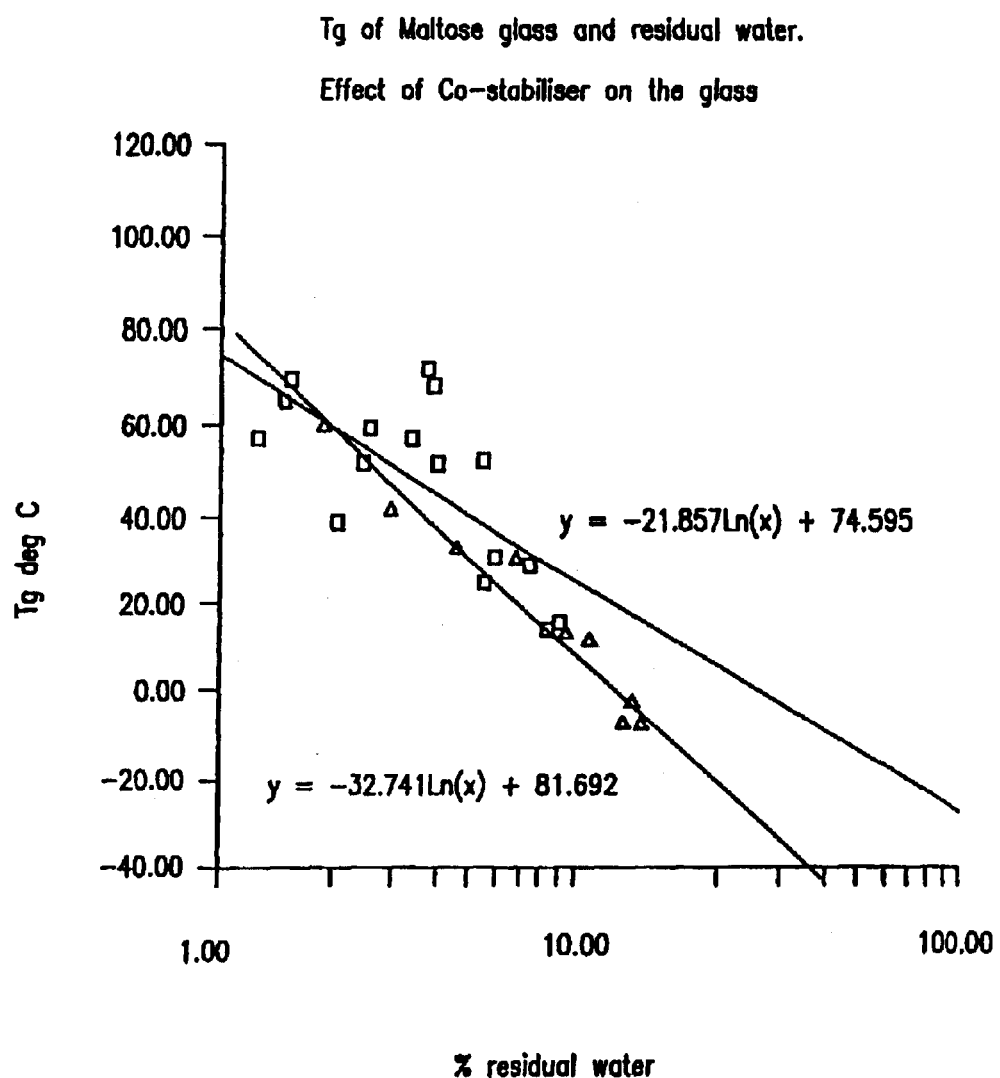
FIG. 8 is a graph depicting the effect of a glass modifier on the Tg of maltose.

The presence of protein in a powdered trehalose glass has now been found to stabilize the glass against the plasticizing effected by water on pure trehalose glasses. This is illustrated by the results depicted in FIG. 7, which show the effect of water on the glass transition temperature of trehalose glasses with (solid line) or without (broken line) bovine serum albumin at concentrations of from 0.002–50%. This effect is not seen or is seen only partially with other carbohydrates, as illustrated by the results depicted in FIG. 8 utilizing maltose.

This elevation of Tg by protein is utilized to formulate trehalose stabilized protein in a pure trehalose glass. A powdered protein-containing trehalose glass is prepared as described in Example 1, added to the melt of a pure trehalose glass and the mixture immediately quenched to give the trehalose-stabilized protein powder in a solid solution in a pure trehalose glass. This glass can then be further processed as described in Examples 1 and 2. A similar embedded glass can be formed if an alternative stabilizing polyol with a Tg lower than that of trehalose is used to form the pure sugar glass, which again allows this glass to be melted and used below the melting point of the powdered, stabilized-protein glass to be embedded. For example, palatinit glasses melt at 60–70° C. at which temperature the protein-stabilized powder is still a glass and the trehalose-stabilized protein glass can thus be encapsulated in the palatinit glass melt by simply mixing and quenching.

EXAMPLE 5

Preparation of Bioactive Material/Stabilizing Polyol Compositions a) Microparticles of trehalose containing MB9 were prepared by spray drying as described in Example 2b. The solution dried contained 0.39 M trehalose and 0.14 M calcium lactate and 0.5% MB9. These particles were coated by adding them to a saturated solution of zinc palmitate ($ZnCl_{16}$) in toluene and cooling from 60° C. to 30° C. This deposited a layer of $ZnCl_{16}$ on the particles which were then filtered under pressure to remove the excess $ZnCl_{16}$, washed with acetone and air-dried. The resulting powder remained unwetted in water for at least three days (the particles floated in the water without sinking or releasing MB9 and thereafter slowly released dye into the water). Thus, otherwise water soluble powders may be made water impermeable by coating with metal carboxylates such as $ZnCl_{16}$ to yield slow release formats. Note that the coating material is most likely in crystalline form and not a glass; therefore, the solid phase in which the bioactive materials are suspended need not be in the glass phase to be impermeable.

b) Coformulation of Carbohydrate and Organic Glasses by Evaporation

A powdered trehalose glass containing phycoerythrin was added to a 1:1 mixture of sodium octanoate and zinc ethylhexanoate dissolved in an excess of chloroform and evaporated under a stream of $N_2$ at room temperature to yield a carboxylate glass containing phycoerythrin powder in solid solution. The coformulated glass remained insoluble in water for at least 48 hrs. The phycoerythrin powder remained fluorescent both in the initial organic solution and in the final glass.

c) Coformulation of Carbohydrate and Organic Glasses by Co-Melting

A preformed organic glass formed by quenching a melt of 1:1 mixture of sodium octanoate and zinc ethylhexanoate was melted at 95° C. and a powdered trehalose glass containing phycoerythrin was added to the melt. The resultant mixture was immediately quenched on an aluminum block precooled to 15° C. A clear carboxylate glass formed containing encapsulated phycoerythrin powder which retained its biological functionality as assayed by its ability to fluoresce. Varying the nature and ratios of the carbohydrate and organic moieties in the coformulated glasses results in glasses with a range of slow-release characteristics as assessed from their variable dissolution times in water.

d) Coformulation of Carbohydrate Glasses and Plastics by Evaporation

A powdered trehalose glass containing phycoerythrin prepared according to Example 1 was added to a solution of perspex filings dissolved in an excess of chloroform and evaporated under a stream of $N_2$ at room temperature to yield a solid perspex block containing the phycoerythrin powder in solid solution. The phycoerythrin powder remained fluorescent both in the initial organic solution and in the reformed solid perspex which was impermeable to water even after 4 weeks. Similar results were obtained with polyester dissolved in dichloromethane and polyurethane dissolved in dimethylsulfoxide.

EXAMPLE 6

Preparation of Hollow Needles Filled with Bioactive Materials

The end of a billet of a trehalose glass tubes with a central cavity filled with a powdered trehalose glass containing phycoerythrin prepared according to Example 1 was melted in a zone furnace and the fiber drawn by winding onto a metal drum rotated at constant speed. The hollow fibers formed contain the finely powdered trehalose-stabilized compound and can be cut to any desired size. The hollow fiber can also be made of thermoplastic, organic glass or carbohydrate which may itself be water soluble, and by varying the diameter of the fibers produced, the filled needles can be formed which vary from micro to macro needles, i.e. from thicknesses of microns to fractions of a millimeter. the hollow needles may be filled with any solid dose vehicle described herein.

EXAMPLE 7

Ballistic Delivery of Solid Dosage Delivery Vehicle

Powdered glasses were injected into the skin by propulsion at hypersonic speeds using a pressure shock wave created by the release of compressed gas. The powder was held in the chamber attached to the large end of a funnel-shaped cavity to the smaller end of which was attached a cartridge of compressed gas sealed by a mylar film and the hypersonic shock wave was generated by rupture of the mylar membrane. Alternatively, a timer relay-driven solenoid can be used to control the helium release which would allow functioning at lower helium pressures. This is the principle used in the particle inflow gun (PIG) developed by Finer for transforming plant tissues. Vain et al. (1993) *Plant Cell Tissue and Organ Culture* 33:237–246.

Although the foregoing invention has been described in some detail by way of illustration and example for purposes of clarity of understanding, it will be apparent to those skilled in the art that certain changes and modifications may be practiced. Therefore, the description and examples should not be construed as limiting the scope of the invention, which is delineated by the appended claims.

We claim:

1. A therapeutic dried composition in solid dose form suitable for oral delivery, comprising a stabilizing polyol and immunogenic agent wherein the composition provides a quick release or flooding dose of the immunogenic agent after administration.

2. The composition, according to claim 1, wherein the composition is freeze-dried.

3. The composition, according to claim 1, wherein the immunogenic agent is selected from the group consisting of live and attenuated viruses, nucleotide vectors encoding antigens, bacteria and antigens.

4. The composition, according to claim 1, wherein the immunogenic agent is an antigen selected from the group consisting of diptheria, tetanus, pertussis, botulinum, cholera, Dengue, hepatitis A, C and B, haemophilus influenzae b, herpes virus, *Hylobacterium pylori*, influenza, Japanese encephalitis, meningococci A, B and C, measles, mumps, papilloma virus, pneumococci, polio, rubella, rotavirus, respiratory syncytial virus, Shigella, tuberculosis, yellow fever and combinations thereof.

5. The composition, according to claim 1, further comprising an amount of adjuvant effective to enhance an immune response to the immunogenic agent.

6. The composition, according to claim 5, wherein the adjuvant is selected from the group consisting of aluminium salts, squalene mixtures (SAF-1), muramyl peptide, saponin derivatives, mycobacterium cell wall preparations, monophosphoryl lipid A, mycolic acid derivtives, nonionic block copolymer surfacants, Quil A, cholera toxin B subunit, polyphosphazene, immunostimulating complexes and mitogenic components of Freund's adjuvant.

7. The composition, according to claim 1, wherein the stabilizing polyol is selected from the group consisting of monosaccharides, disaccharides, trisaccharides, oligosaccharides.

\* \* \* \* \*

UNITED STATES PATENT AND TRADEMARK OFFICE
CERTIFICATE OF CORRECTION

PATENT NO.    : 6,893,657 B2
DATED         : February 27, 2003
INVENTOR(S)   : Bruce J. Roser et al.

It is certified that error appears in the above-identified patent and that said Letters Patent is hereby corrected as shown below:

Title page,
Item [*] Notice, should read -- This patent is subject to a terminal disclaimer. --.

Column 20,
Line 16, "C and B" should read -- C and E --.

Signed and Sealed this

Twenty-third Day of August, 2005

JON W. DUDAS
*Director of the United States Patent and Trademark Office*

UNITED STATES PATENT AND TRADEMARK OFFICE
CERTIFICATE OF CORRECTION

PATENT NO.    : 6,893,657 B2
DATED         : May 17, 2005
INVENTOR(S)   : Bruce J. Roser et al.

It is certified that error appears in the above-identified patent and that said Letters Patent is hereby corrected as shown below:

Title page,
Item [*] Notice, should read -- This patent is subject to a terminal disclaimer. --.

Column 20,
Line 16, "C and B" should read -- C and E --.

This certificate supersedes Certificate of Correction issued August 23, 2005.

Signed and Sealed this

Eighteenth Day of October, 2005

JON W. DUDAS
*Director of the United States Patent and Trademark Office*